US007674478B2

(12) United States Patent
Kataoka et al.

(10) Patent No.: US 7,674,478 B2
(45) Date of Patent: *Mar. 9, 2010

(54) POLYMER MICELLE AS MONOLAYER OR LAYER-LAMINATED SURFACE

(75) Inventors: Kazunori Kataoka, Tokyo (JP); Yukio Nagasaki, Moriya (JP); Kazunori Emoto, Huntsville, AL (US); Michihiro Iijima, Oyama (JP)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/653,626

(22) Filed: Sep. 2, 2003

(65) Prior Publication Data
US 2005/0079197 A1 Apr. 14, 2005

Related U.S. Application Data

(62) Division of application No. 09/705,349, filed on Nov. 3, 2000, now abandoned.

(30) Foreign Application Priority Data

Nov. 4, 1999 (JP) .................................. 11-313457
Nov. 4, 1999 (JP) .................................. 11-313463

(51) Int. Cl.
*A61K 9/133* (2006.01)
(52) U.S. Cl. .................................................. 424/429
(58) Field of Classification Search ................ 424/423, 424/426, 427, 428, 450
See application file for complete search history.

(56) References Cited

U.S. PATENT DOCUMENTS

| 4,749,585 | A |   | 6/1988 | Greco et al. |
| 5,135,297 | A | * | 8/1992 | Valint, Jr. ................. 351/160 R |
| 6,107,102 | A | * | 8/2000 | Ferrari ........................ 436/518 |
| 7,037,517 | B2 | * | 5/2006 | Kataoka et al. ............. 424/427 |

FOREIGN PATENT DOCUMENTS

| EP | 0 822 217 A1 | 2/1998 |
| EP | 0 844 269 A1 | 5/1998 |
| WO | WO 96/38726 | 12/1996 |
| WO | WO 99/26665 | 6/1999 |

OTHER PUBLICATIONS

Emoto, K. et al., "Coating of Surfaces with Stabilized Reactive Micelles from Poly(ethylene glycol)- Poly(DL-lactic acid) Block Copolymer," *Langmuir*, 15: 5212-5218 (1999).
Emoto, K. et al., "A Core-Shell Structured Hydrogel Thin Layer on Surfaces by Lamination of a Poly9ethylene glycol)-b-poly(D,L-lactide) Micelle and Polyallylamine", *Langmuir*, 16: 5738-5742 (2000).
Emoto, et al. "Functionality of Polymeric Micelle Hydrogels with Organized Three-Dimensional Architecture on Surfaces", *J. Am. Chem. Soc.,* 122: 2653-2654 (2000).

* cited by examiner

*Primary Examiner*—Carlos A. Azpuru
(74) *Attorney, Agent, or Firm*—Scully, Scott, Murphy & Presser, P.C.

(57) ABSTRACT

The present invention is directed to a coated biomedical device said micelle having a hydrophilic outer shell and a hydrophobic inner core, or a hydrophobic outer shell and a hydrophilic inner core said micelle comprised of a block copolymer having a HLB value ranging from about 1 to about 40. The medical device may have one coating thereon or multiple coatings. The present invention is also directed to the use of the micelle as a drug carrier.

28 Claims, 6 Drawing Sheets

POLYMER MICELLE AS MONOLAYER OR LAYER-LAMINATED SURFACE

RELATED APPLICATION

This application is a divisional application of application U.S. Ser. No. 09/705,349, now abandoned, filed on Nov. 3, 2000.

FIELD OF THE INVENTION

The present invention relates to a polymer micelle which is either in a single layer or in multi-layers and to the use thereof as a coating on surfaces, especially biomedical devices.

BACKGROUND OF THE INVENTION

A micelle is a colloidal aggregate of amphipathic molecules containing both hydrophilic and hydrophobic moieties. In polar media, such as water, the hydrophobic part of the amphiphile forming the micelle tends to locate away from the polar portion, while the polar portion of the molecule also known as the head group tends to locate at the polar micelle water (solvent) interface. On the other hand, micelles may also be formed in non-polar media, such as non-polar organic solvents, e.g., hexane, whereby the amphiphilic cluster around the small water droplets is in the center of the system. In non-polar media, the hydrophobic moieties are exposed to the non-polar media, while the hydrophilic portion tends to locate away from the solvent and towards the water droplets. Such an assembly is sometimes referred to as a reversed micelle. These two aforementioned systems represent water-in-oil and oil-in-water, respectively, types of systems.

A micelle may take several forms, depending on the conditions and the composition of the system. For example, small micelles in dilute solution at approximately the critical micelle concentration (CMC) are generally believed to be spherical. However, under other conditions, they may be in the shape of distorted spheres, disks, rods, lamellae, and the like.

Micelles are formed at a critical micelle concentration (CMC) which is dependent upon several factors, including the type of amphipathic molecule, the solvent system, solute and the like. The critical micelle concentration denotes the concentration at which micelles start to form in a system containing solvent, amphipathic molecule, and solute and the like. The CMC can be determined experimentally using standard techniques in the art. For example, the CMC of a surfactant can be determined by plotting a property as a function of the concentration of the surfactant; it is noted that the property usually varies linearly with increasing concentration up to the CMC, at which point the curve becomes non-linear. Properties which have been used for the determination of the CMC include such properties as refractive index, light scattering, dialysis, surface tension and dye solution.

Micellar properties are affected by the environment and more specifically changes in the environment, e.g., temperature, solvents, solubilized components, electrolytes in the system and the like. The prior art has described micelles whose properties have been exploited.

For example, U.S. Pat. No. 5,929,177 to Kataoka, et al. describes a polymeric molecule which is usable as, inter alia, a drug delivery carrier. The micelle is formed from a block copolymer having functional groups on both of its ends and which comprises hydrophilic/hydrophobic segments. The polymer functional groups on the ends of the block copolymer include amino, carboxyl and mercapto groups on the α-terminal and hydroxyl, carboxyl group, aldehyde group and vinyl group on the ω-terminal. The hydrophilic segment comprises polyethylene oxide, while the hydrophobic segment is derived from lactide, lactone or (meth)acrylic acid ester.

U.S. Pat. No. 5,925,720 to Kataoka, et al. provides a heterotelechelic oligomer or polymer of the formula:

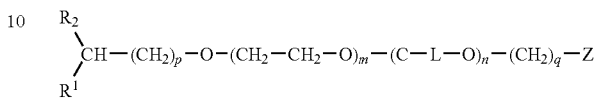

wherein
$R^1$ and $R^2$ combined with each other denoted $C_{1-10}$ alkoxy, aryloxy or aryl $C_{1-3}$ alkoxy or oxy (=O), or $R^1$ and $R^2$ independently denote ethylenedioxy, O—CH($R^1$)—CH$_2$—O—;
$R^1$ denotes hydrogen or $C_{1-6}$ alkyl;
L is

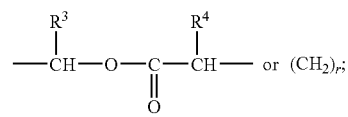

$R^3$ and $R^4$ independently denote hydrogen, alkyl, aryl or arylalkyl;
r is 2-5;
m is 2-10,000;
n is 2-10,000;
p is 1-5;
q is 0-20;
when q is 0, Z denotes H, alkali metal, acetyl, acryloxyl, methacryloyl, cinnamoyl, p-toluenesulfonyl, 2-mercaptopropionyl or 2-aminopropionyl or allyl or vinylbenzyl,
when q is 1-20, Z is $C_{1-6}$ alkoxycarbonyl, carboxyl, mercapto or amino.

This oligomer or polymer forms a high-molecular micelle which is stable in aqueous solvent and is useful as a carrier for drug delivery.

In neither of these references was the micelle used as a coating.

However, other types of non-micellar polymers have been used to coat surfaces. For example, U.S. Pat. No. 5,275,838 to Merrill discloses a method for immobilizing polyethylene oxide (PEO) stat molecules in the form of hydrogel layers and the product thereof which can be used to coat surfaces. It describes a method for immobilizing polyethylene oxide star molecules to a support surface to form a layer thereon, comprising the steps of:

(a) exposing an organic solution comprising polyethylene oxide star molecules, each of which consists essentially of a plurality of hydroxy terminated polyethylene oxide chains to a divinyl benzene core, to a reagent to affix reagent groups to the hydroxy termini, said reagent groups permitting subsequent attachment of amino or thiol groups to the PEO chain ends by displacement, thereby forming activated polyethylene oxide star molecules with active reagent end groups;

(b) separating the activated polyethylene oxide star molecules with active reagent end groups from the organic solvent;

(c) dissolving the activated polyethylene oxide star molecules in an aqueous solution; and (d) contacting the solution of step (c) with a support surface containing amino and/or thiol groups to covalently bond the reagent terminated star molecules, thereby immobilizing the reagent terminated star molecules in a dense layer to the support surface.

The star molecules have a polymeric core, such as divinyl benzene, from which a number of polyethylene oxide chains or arms are grown. These star molecules are not micelles. They are not comprised of block copolymers having HLB (hydrophilic-lipophilic balance) of 1-40. As described therein, the star molecules are synthesized by anionic polymerization from divinyl benzene, ethylene oxide and optionally styrene.

The present invention utilizes different types of compounds and coating technology than those described in Merrill. Unlike Merrill, the coating composition of the present invention are comprised of micelles. As explained hereinbelow, the micelles utilized in the present invention are comprised of block copolymers having an HLB value ranging from 1-40. The present inventors have found coating a surface with specific polymeric micelles of the present invention imparts several advantages to the coated surface. More specifically, the present inventors have found that coated surfaces, especially multi-layered coated surfaces, with polymeric micelles of the type described hereinbelow enhances the ability of the coated surface to retain water, prevents penetration of proteins and lipids therethrough and enhances drug delivery capabilities of the coated surface.

SUMMARY OF THE INVENTION

Accordingly, the present invention is directed to a coated support surface, such as a biomedical device, wherein the coating comprises at least one polymeric micelle immobilized on the surface of said biomedical device, said micelle having either a hydrophilic outer shell and an hydrophobic inner core or a hydrophobic outer shell and a hydrophilic inner core, said micelle comprised of a block copolymer having a HLB value ranging from about 1 to about 40. The polymer micelle used to coat the support surface may be present as a monolayer. Alternatively, they may be multilayers in which the various layers are crosslinked to each other. In another embodiment, the multi-layer micelle contains at least two polymer micelles sandwiching either a high molecular weight polymer compound having a number of functional groups or a multi-functional low-molecular weight polymer compound having at least two functional groups.

| ○ | ML2 | ■ | 3LE |
|---|---|---|---|
| ● | ML16 | ▲ | 6LR |
| □ | 3LO | | |

Figure 6:
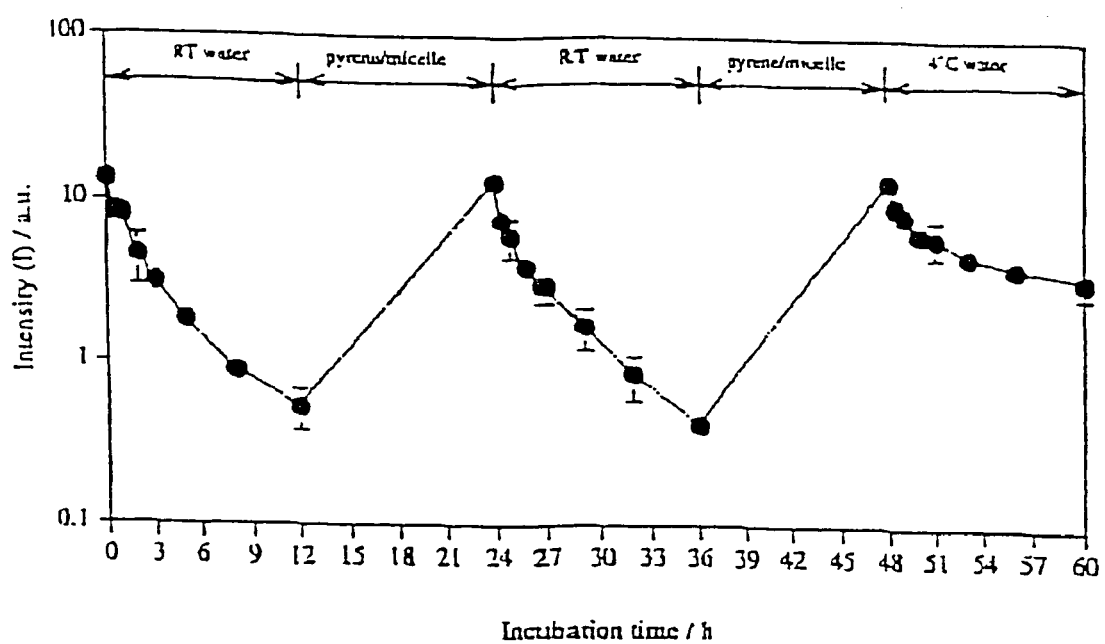

FIG. 6 graphically depicts the change in fluorescence intensity (I) of APTS glass coating with 6-layer of polymerized micelles after exposure to pyrene/micelle solution and water.

Figure 7:
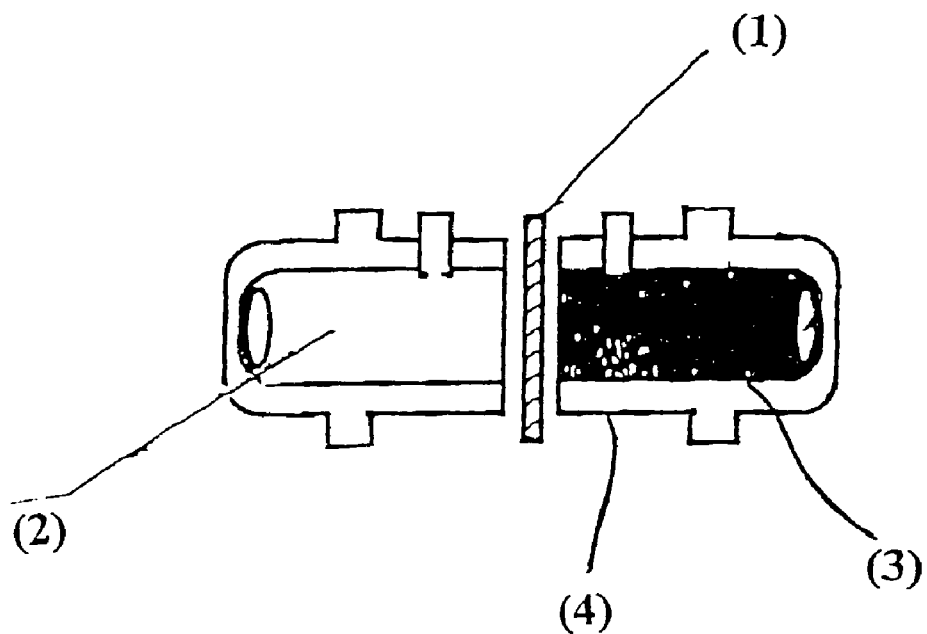

FIG. 7 schematically depicts the chamber to test the migration of dextran through the film coated with micelle, as described in Example 3.

Figure 8:
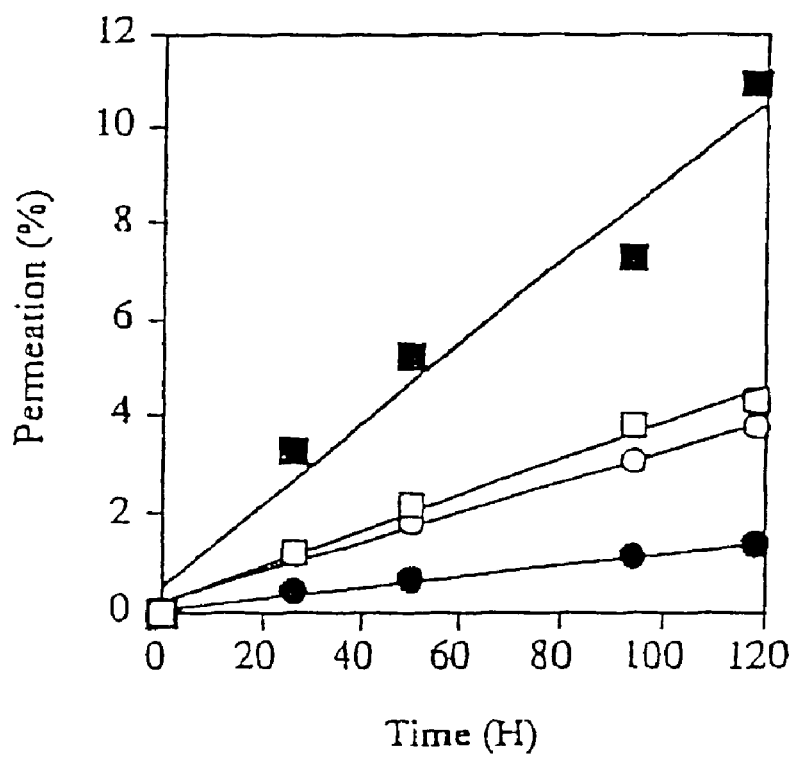

FIG. 8 shows the plot of the permeation of dextran through the micelle coated films, as described in Example 6. In the graph, the following legend is utilized:
□ PHEMA/polypropylene film
■ PHEMA/polypropylene film coated with PEG-aldehyde (MW 5000)
○ Monolayer micelle
● layer micelle

DETAILED DESCRIPTION OF THE PRESENT INVENTION

As described herein, the present invention relates to a support surface coated with the polymer micelle of the present invention.

As used herein, the term "support surface" is a product which is likely to be brought into contact with biological fluid when used. Biological fluid means a body fluid of animals like human being, such as tears, blood, urine, sweat and saliva. Representative examples include biomedical devices, such as artificial organs (e.g., artificial heart, artificial blood vessel, artificial bone, pacemaker, etc.), contact lens, stints, diagnostic instrument (e.g., catheter), storage vessel for body fluid, and experiment ware used in the laboratory (e.g., test tube, beaker, etc.). Furthermore, the support surface may be a film-like structure which is made of high-molecular weight compounds laying between polymer micelles. The term "film-like" means that the substrate does not necessarily need to be a continuous film all through the structure. In addition, the support surface may be a pharmaceutically acceptable carrier.

It is preferred that the support surface is a biomedical device; the most preferred biomedical device is a contact lens and intraocular lens.

As used herein the term "support surface" refers to both the untreated surface on which the micelle is immobilized, as well as the surfaces which have been treated, coated or modified to enhance or promote an immobilization of the micelle thereon. It is preferred that the micelle is immobilized to the biomedical device through a covalent bond. For example, as illustrated hereinbelow, some surfaces may have hydroxy groups thereon, the micelle having carboxylic acid or carboxylic acid esters thereon can react under ester forming conditions to form an ester in which a covalent bond is formed between the oxygen atom on the surface with the acyl group of the micelle. On the other hand, the surface may be modified or treated to form a covalent bond with the micelle and the surface so treated is encompassed within the term "support surface". For example, if the surface has hydroxy groups, the support may be placed in a bath of an inert solvent, such as tetrahydrofuran, and tresyl chloride. The hydroxy groups on the surface are then tresylated. Once tresylated, the support surface may be aminated in a water solution of ethylene diamine, which results in bonding the group —NH—CH—$CH_2$—$NH_2$ to the carbon atom thereon which was bonded to the displaced hydroxy group thereon. Unreacted diamine is removed and then the surface so treated is reacted with the carboxylic acid groups thereon under amide forming conditions to form an amide so that a covalent bond is formed between the modified surface having the amino group and the aryl group of the micelle. Moreover, the surface may be coated with a non-micelle coating that contains amino groups thereon, and the amino groups on the coat can react with the carboxylic acid groups of the micelle. Thus, a modification of the surface by placing a coating on the surface is included within the term "surface", when defining the immobilization and/or formation of a covalent bond between the support surface and the micelle.

The immobilization between the support surface and the micelle is preferably a covalent bond linkage therebetween as described herein.

The coating may be one layer or may be more than one layer or multi-layered. As used herein the term "multilayer" refers to two or more layers. If it is more than one layer, it is preferred that it contains at least two layers and more preferably 2-10 layers and even more preferably 2-6 layers. It is preferred that the coating comprises a multi-layered micelle.

The polymer micelle forming the coat has a predetermined thickness regardless of whether a monolayer or a multilayer is utilized. The monolayer preferably has a thickness on the order of magnitude of greater than 0.05 microns and more preferably the thickness of the monolayer ranges from about 0.1 microns to about 0.5 microns and most preferably from about 0.1 microns to about 0.3 microns.

When multi-layered, each micelle layer may have the same or a different thickness than the other layers of the composite. Within each layer, however, the thickness is preferably uniform. The term "hydrogel" is a term of art and refers to a broad class of polymeric materials which are swollen extensively in water, but which do not dissolve in water. The thickness of each layer, however, is usually determined by the various groups present in the micelle, such as the functional groups thereon, the high molecular polymer compound or the low molecular compound that may be present, the hydrophilic group and the like.

If the micelle is a monolayer, it may be comprised of one polymeric micelle or more than one polymeric micelle, although it is preferred that it is comprised of one polymeric micelle. If multilayered, the various layers may be comprised of one polymeric micelle or more than one polymeric micelle. Moreover, even within each layer, there may be one or a mixture of more than one polymeric micelles. However, it is preferred that each layer is comprised of one type of polymeric micelle.

In an embodiment of the present invention, the coated biomedical device is coated with a monolayer of the micelle. For example, in an embodiment, the biomedical device is coated with a multi-layer of micelles. In an embodiment where the biomedical device is coated with multi-layer of the micelle, the multi-layer comprises at least one set of covalently bonded layers comprised of two polymer micelles and a second polymer sandwiched therebetween, the second polymer having a molecular weight greater than 8000 daltons and having a plural number of functional groups thereon selected from the group consisting of an amino group, a carboxyl group, and a sulfo group. In this embodiment, the second polymer is, for example, polyallylamine, polyvinylamine, polylysine, chitosan, polyethyleneimine, poly (meth) acrylic acid, carboxymethylcellulose, alginic acid, heparin, or polystyrene sulfonic acid. Thus, in an embodiment, the biomedical device is coated with a multi-layer polymer micelle wherein the multi-layer comprises at least one set of covalently bonded layers comprised of two polymer micelles and sandwiched therebetween is a low molecular weight molecule selected from the group consisting of lower alkylene diamine, glutaraldehyde and ethanedithiol.

In a preferred embodiment, the present invention is capable of providing a surface which supports a hydrogel layer of desired thickness by means of choosing the number of lamination of polymer micelle layers. It is preferred that if laminated, there is no more than 10 layers on the support surface and more preferably up to and including 6 layers. In an embodiment, the present invention contemplates a coated biomedical device wherein the coating comprises at least one polymeric micelle immobilized onto the surface of the biomedical device, the micelle having a hydrophilic core and hydrophobic shell or a hydrophobic core and a hydrophilic shell, the micelle comprised of a block copolymer having a HLB value ranging from about 1 to about 40. In another embodiment, the biomedical device is coated with at most six layers of the micelle. Nevertheless, it is preferred that the thickness of each layer be greater than 0.05 microns and more preferably, the thickness of each layer in the multilayer embodiment ranges from about 0.05 microns to about 0.5 microns, and more preferably from about 0.05 microns to about 0.1 microns.

The thickness of the polymer micelle monolayer or multilayer can be regulated by various techniques known in the art, such as doctor-blade spreading on a support web or centrifugal casting in tubes.

As contemplated herein in one embodiment of the present invention, the micelle has a outer hydrophilic shell and an inner hydrophobic core. Under these circumstances, the linkage between the support surface and the micelle is preferably a covalent bond between the hydrophilic shell and the support surface.

Alternatively, the micelle may have a hydrophobic outer shell and a hydrophilic inner core, i.e., a reverse micelle. Under these circumstances, the linkage between the support surface and the micelle is, preferably, a covalent bond between the hydrophobic outer shell and the support surface. If the micelle is a reverse micelle, it is preferred that a multi-layered micelle is formed in which the reverse micelle layer with the outer hydrophobic shell sandwiches a normal micelle, i.e. one in which the outer layer is hydrophilic and the inner layer is hydrophobic. This forms a stable interaction between the various layers, since the hydrophilic inner cores of the reverse micelles face the hydrophilic outer shell of the normal micelle and do not face or interact with the hydrophobic inner core of the normal micelle.

As used herein, unless indicated to the contrary, the term "micelle" shall include "normal micelle" and "reverse micelle". As noted herein, the term "normal micelle" is a micelle in which the micelle has a hydrophilic outer shell and a hydrophobic inner core, while a reverse micelle has the opposite, i.e., a hydrophobic outer shell and a hydrophilic inner core.

As indicated hereinabove, the present invention is directed to a coated support, preferably a coated biomedical device, wherein the coating comprises at least one polymeric micelle covalently bonded to the surface of the biomedical device, said micelle being immobilized on the support surface. It is preferred that the micelle is bonded to the support surface. It is also preferred that the micelle has a hydrophilic outer shell which is covalently bonded to the surface of the biomedical device and a hydrophobic inner core, although reverse micelles in which the hydrophobic outer shell is covalently bonded to the support surface is also contemplated within the scope of the invention.

In an embodiment, in the coated biomedical device of the present invention, the hydrophobic core has at its terminus a free radical reactive group. For example, in an embodiment, the hydrophobic shell has at its terminus an ethyleneically polymerizable group. Examples of the ethyleneically unsaturated polymerizable group include a free radical reactive polymerizable acrylate, free radical reactive polymerizable styryl, free radical reactive polymerizable methacrylate and a free radical polymerizable vinyl ethyl ether. In another embodiment the present invention is directed to a biomedical device wherein the hydrophilic core has at its terminus end a free radical reactive group. In an embodiment of the present invention, in the coated biomedical device, the hydrophilic shell has at its terminus end an ethyleneically unsaturated polymerizable group. Examples of the ethyleneically unsaturated polymerizable group include a free radical reactive polymerizable acrylate, free radical reactive polymerizable styryl, free radical reactive polymerizable methacrvlate and a free radical polymerizable vinyl ethyl ether.

Regardless whether a normal or reverse micelle is utilized, said micelle is comprised of a block copolyiner having a HLB value ranging from about 1 to about 40.

HLB (hydrophilic-lipophilic balance) is a term of art that is quite familiar to one of ordinary skill in the art. It refers to the amount of hydrophilic and lipophilic moieties present in a non-ionic molecule. Its definitions and application are described in "The HLB system", promoted by ICI Americas, Inc.

Block copolymers, which are surface active, are classified by the ratio of the hydrophilic and lipophilic segments in the molecule. A large number of commercial emulsifying agents, such as surfactants, have been assigned a hydrophilic/lipophilic balance (HLB) number. In some cases, the number is calculated from the structure of the molecule and in others, it is calculated based on experimental emulsification data. Alternatively, HLB numbers have been evaluated by other methods, e.g., cloud points, gas chromatography, critical micelle concentrations and NMR spectroscopy. It is preferred that the HLB value is calculated using the structural approach. A commonly used general formula for determining the HLB value of a nonionic material, including micelles, is:

$$20 \times (M_H)/(M_H + M_L) \quad \text{EQ I}$$

wherein $M_H$ is the formula weight of the hydrophilic segment and $M_L$ is the formula weight of the hydrophobic segment. For example, a block copolymer utilized in the present invention having the formula:

T-[Ethylene oxide]$_{35}$-[Methylmethacrylate]$_{28}$-U where

T and U are anchors to the support, has a HLB=(20)[1540/(1540+2800)]=7.1.

Unless indicated to the contrary, the HLB values referred to hereinabove refer to the HLB value obtained via a structural approach and more precisely by the calculation of EQI, as described hereinabove.

In a preferred embodiment, the block copolymer utilized in the present invention has a HLB value ranging from about 4 to about 20.

The block copolymer and the resulting micelle therefrom consists of a hydrophilic moiety (water soluble) and a hydrophobic moiety. It is preferred that the micelle has a hydrophilic outer shell and a hydrophobic inner core.

The preferred water soluble (hydrophilic) region of the block copolymer and micelle consists of polyethylene glycol, polyethylene oxide, polyvinyl alcohol, polyacrylamide, polymethacrylamide, poly(vinylpyrrolidone), and the like. It is most preferred that the hydrophilic moiety is polyethylene glycol, polyacrylamide, polymethacrylamide, poly(vinylpyrrolidone) or polyvinyl alcohol. The most preferred hydrophilic core is polyethylene glycol.

The hydrophobic polymer segment is attached to the hydrophilic polymer by non-hydrolyzable chemical bonds, such as carbon-carbon bonds, by amide linkage, ether linkages, ester linkages, thio linkages, amino linkages, and the like.

The hydrophobic polymer segment utilized herein may be derived from any polymer provided that the corresponding block copolymer forms a stable polymer micelle when dissolved or dispersed in a solvent which is capable of dissolving said hydrophobic polymer segment. The preferred hydrophobic polymer segments include poly($\alpha$-hydroxycarboxylic acids) which are derived from either glycolide or lactide; poly($\omega$-hydroxycarboxylic acids) which are derived from either $\gamma$-lactone or $\delta$-lactone or $\epsilon$-lactone; or those derived from a copolymer of such poly($\alpha$-hydroxycarboxylic acids) with such poly($\omega$-hydroxycarboxylic acids). The hydrophobic polymer segments may have an ethylenically unsaturated polymerizable group at one end which is opposite to the one at which the hydrophobic polymer segment is bonded to the hydrophilic polymer segment. Such a polymerizable group can be introduced from. (meth)acrylic acid or vinylbenzyl chloride. Furthermore, such a polymerizable group may be subjected to a polymerization reaction after the formation of the polymer micelle, and is thus brought into a polymerized (crosslinked) state with the support surface. In such a state, the polymer micelle per se is more stable.

The hydrophilic polymer segment, on the other hand, has a functional group at an end opposite to the one at which it is bonded to the hydrophobic polymer segment. Hence, in a preferred embodiment when the block copolymer forms a polymer micelle, said functional group exists on the surface, or near the surface, of said polymer micelle, thereby forming a normal micelle. This functional group is preferably used to covalently bond the polymer micelle with the support surface and, when present, the high-molecular weight polymer compound or multi-functional low-molecular weight compounds lying between the polymer micelles. The hydrophilic and hydrophobic polymer segments on the micelle may have more than one functional group and the functional groups may be the same or different. Examples of the functional groups present on the block copolymer include aldehyde groups, carboxyl groups, hydroxyl groups, mercapto groups, amino groups and the like. If the high molecular weight polymer compound or multi-function low molecular weight compound is present, they have functional groups, some of which may bind to the polymeric micelle. These various functional groups thereon may be the same or different and they may be the same or different from the functional groups present on the hydrophilic or hydrophobic portion of the micelle.

The most preferred polymer micelle is formed from a block copolymer which is composed of both a hydrophilic polymer segment essentially comprising poly(ethyleneglycol) [hereinafter sometimes abbreviated as PEG] and a hydrophobic polymer segment. The phrase "essentially comprising"

means that PEG occupies the main portion of the hydrophilic polymer segment, and that some linking group or the like which has essentially no influence on the hydrophilicity of said segment may be contained in some amount in the PEG chain or between hydrophilic and hydrophobic polymer segments. However, it is preferable that the PEG chain consists of PEG alone.

Examples of block copolymers from which micelles of the present invention can be prepared which can be used to coat a support surface are found in U.S. Pat. No. 5,925,720, to Kataoka, et al., U.S. Pat. No. 5,412,072 to Sakarai, et al., U.S. Pat. No. 5,410,016 to Kataoka, et al., U.S. Pat. No. 5,929,177 to Kataoka, et al., U.S. Pat. No. 5,693,751 to Sakurai, et al., U.S. Pat. No. 5,449,513 to Yokoyama, et al., WO 96/32434, WO 96/33233 and WO 97/0623, the contents of all of which are incorporated by reference. Modifications thereof which are prepared by introducing thereon a suitable functional group (including an ethyleneically unsaturated polymerizable group) are also examples of block copolymers from which micelles of the present invention are preferably prepared. Preferable block copolymers are those disclosed in the above-mentioned patents and or international patent publications. If the block copolymer has a sugar residue on one end of the hydrophilic polymer segment, as in the block copolymer of WO 96/32434, the sugar residue should preferably be subjected to Malaprade oxidation so that a corresponding aldehyde group may be formed.

Examples of block copolymers are shown by formulae (I), (II) or (III) below:

Formula (I)

$$HC-(CH_2)_p-O-(CH_2CH_2O)_m-(C-L-O)_n-Z$$
$$\parallel \qquad\qquad\qquad\qquad\qquad \parallel$$
$$O \qquad\qquad\qquad\qquad\qquad\qquad O$$

wherein
L denotes compounds of the following formula:

$$-CH-O-C-CH-$$
$$\;\;|\;\;\qquad\;\;\parallel\;\;\qquad|$$
$$R^1\qquad\;\;O\qquad R^2$$

or $-(CH_2)_r-$ wherein
$R^1$ and $R^2$ independently denote hydrogen atom, $C_{1-10}$ alkyl, aryl or aryl-$C_{1-3}$ alkyl; r denotes an integer of 2-5, and wherein
m denotes an integer of 2-10,000;
n denotes an integer of 2-10,000;
p denotes an integer of 1-5; and
Z denotes acetyl, acryloyl, methacryloyl, cinnamoyl, allyl or vinylbenzyl;

or the following Formula (II)

$$X-(CH_2CH_2O)_m-(Y)_n-Z \qquad\qquad (II)$$

wherein
X denotes an alkyl group having 1 to 10 carbon atoms which has an amino group, a carboxyl group or a mercapto group;

Y denotes groups of the following formula:

$$-CCHOCCHO-,\qquad -C(CH_2)_q-O-,$$
$$\parallel\;\;|\;\;\parallel\;\;|\qquad\qquad\;\;\parallel$$
$$O\;R^{11}\;O\;R^{12}\qquad\qquad O$$

$$-CH_2C-\qquad\;\; or\;\;\qquad -CH_2C-$$
$$\qquad|\qquad\qquad\qquad\qquad\qquad|$$
$$\;\;COOR^4\qquad\qquad\qquad\;\; CN$$

(with $R^3$ on each)

wherein
$R^{11}$ and $R^{12}$ independently denote a hydrogen atom or a $C_{1-5}$ alkyl;
$R^3$ denotes a hydrogen atom or a methY$_1$ group;
$R^4$ denotes a $C_{1-5}$ alkyl substituted by a hydroxyl group which may be protected; and
q denotes an integer of 2-5, and wherein
Z denotes acryloyl, methacryloyl, cinnamoyl, allyl or vinylbenzyl; m denotes an integer of 2-10,000; and
n denotes an integer of 2-10,000;
or the following formula (III):

$$A-(CH_2CH_2O)_{n-1}-(C-L_1-O)_m-Z \qquad\qquad (III)$$
$$\qquad\qquad\qquad\qquad\;\;\parallel$$
$$\qquad\qquad\qquad\qquad\;\;O$$

wherein
A denotes a group which is derived, by Malaprade oxidation, from a sugar residue having the following formula:

$$CH-CH\qquad HC-CH-(CH)_b-CH_2O----$$
$$|\qquad\parallel\qquad\qquad\parallel\qquad\qquad|$$
$$(CH_2)_a\;\;O\qquad\;\; O\qquad\qquad OH$$
$$|$$
$$----O$$

(with O bridging top)

wherein
one of the broken lines ( - - - ) denotes a single bond while the other denotes a hydrogen atom; and
a and b independently denote an integer of 0 or 1, and wherein
$L_1$ denotes linking groups of the following formula:

$$-CH-O-C-CH-$$
$$\;\;|\;\;\qquad\;\;\parallel\;\;\qquad|$$
$$R^5\qquad\;\;O\qquad R^6$$

or $-(CH_2)_4-$ wherein
$R^5$ and $R^6$ independently denote a hydrogen atom, a $C_{1-6}$ alkyl, an aryl or a $C_{1-3}$ alkyl aryl; and wherein m denotes an integer of 2-10,000;

n denotes an integer of 2-10,000; and

Z denotes acryloyl, methyacryloyl, cinnamoyl, allyl or vinylbenzyl.

As used herein, unless denoted to the contrary, alkyl group when used alone or in combination with another group refers to a lower alkyl which contains one to six carbon atoms. The carbon atoms may be straight-chained or branched. Examples include methyl, ethyl, propyl, isopropyl, butyl, sec-butyl, isobutyl-t-butyl, pentyl, neopentyl, hexyl and the like.

The term alkenyl, when used alone or in combination with other groups, refers to a loweralkenyl group containing 2-6 carbon atoms. The alkenyl group may contain 1 or more carbon-carbon double bonds up to a maximum of 3; however, it is preferred that it contains 2 and more preferably 1 carbon-carbon double bond. The alkenyl groups may be straight chained or branched. Examples include ethenyl, 1-propenyl, 2-propenyl and the like.

Aryl when used herein, either alone or in combination with another group denotes an aromatic moiety containing only ring carbon atoms and containing $2k+2$ ring carbon atoms, where k is 1, 2, 3 or 4. The aryl group may be monocyclic, bicyclic, tricyclic or tetracyclic; if it contains more than one ring, the rings are fused to one another. The aryl groups may be substituted by lower alkyl group. Thus, the aryl groups may contain 6-18 ring carbon atoms and a total of 6-25 carbon atoms. Examples include phenyl, tolyl, xylyl, naphthyl, α-naphthyl and the like.

From the above-mentioned block copolymers, the polymer micelle is preferably formed where the functional group at the end of the hydrophilic polymer segment is protected (e.g., in the case of aldehyde group, it is acetalized or ketalized; in the case of an amino group, it is protected by an amino protecting group), and, then is subjected to a deblocking reaction. When an ethylenically unsaturated polymerizable group is present at the end of hydrophobic polymer segment, each block copolymer may be subjected to polymerization-crosslinking via said polymerizable group after the polymer micelle is formed.

If the coating of the polymer micelle is a monolayer, then it preferably comprises the components of Formula I-III described hereinabove. If the coating is laminated, then the coating preferably comprises at least one set of layers composed of two polymer micelle layers, formed from at least one of the polymer micelles of Formula I-III described herein.

The laminated layers of a micelle may be crosslinked by carbon-carbon bonds. For example, the micelles may contain interior carbon-carbon double bonds or the side chains thereof may contain carbon-carbon double bonds. The micelles can be cross-linked together by exposing them to electron beam radiation which creates free radicals. Random coupling then results in the formation of a layer. Typically, the solution is exposed to sufficient electron radiation to effect free radical formation. For example, the electron radiation may range from about one to about 10 megarads. Alternatively, the micelles may be cross-linked together by adding a photoinitiator to the micelles in an inert solution, and exposing the solution to visible or UV light of sufficient wavelength to form a free radical. Random coupling then results in the formation of a layer. Typically, the photoinitiator is exposed to sufficient wavelength of light to form free radical which in turn reacts within the micelle, especially the carbon-carbon double bonding to effect free radical formation in the micelles.

Alternatively, the layers may be covalently bonded either with a high-molecular weight polymer compound having one or more functional groups ("another species of" functional group) which groups are covalently bondable with the functional group in the block copolymer in the polymer micelle, or with a multi-functional low-molecular weight compound having at least two, preferably 2 or 3, of said "another species of" functional group, both of said high-molecular weight polymer compound and multi-functional low-molecular weight compound lying intermediate between said two polymer micelle layers. The various layers are, in turn, bonded to each other via a covalent bond between a functional group on the above-mentioned "another species of" functional group of the high-molecular weight polymer compound or multi-functional low-molecular weight compound, and the functional group of the block copolymer in the polymer micelle. Alternatively, the outermost layer may be a layer of the above-mentioned high-molecular compound and in this case, it is bonded to the surface support at one end and the micelle layer via a covalent bond at the other end. A functional group in the support surface is reactive with a functional group on the high molecular weight polymer and a covalent bond is formed between the support surface and the high molecular weight polymer. Moreover, a functional group on the micelle reacts with a functional group at the opposite end of the high molecular weight polymer reactive therewith and forms a covalent bond therebetween.

Examples of functional groups substituted on the high molecular weight compound include an amino group which is covalently bondable with aldehyde (Schiff base which is formed from aldehyde group and amino group may further be reduced); an hydroxyl group and an amino group which are covalently bondable with carboxyl group; a carboxyl group and a sulfo group which are covalently bondable with hydroxyl group; or a mercapto group which is covalently bondable with amino group. Such a covalent bond can be formed under known reaction condition such as oxidation-reduction conditions, dehydration condensation conditions, addition condition, and substitution (or displacement) conditions.

The high molecular weight polymer compound is a polymer having a molecular weight greater than about 8000 daltons and more preferably greater than about 10,000 daltons having amino, carboxyl, thio or sulfo functional groups. It is preferable that the high molecular weight polymer has a molecular weight of less than about 500,000 daltons and more preferably less than about 300,000 daltons.

The above-mentioned high-molecular weight polymer compound is either a natural product or a synthesized one. Examples of those having an amino group include polyalkenylamine, such as polyallylamine, polyvinylamine and the like; polymers of basic amino acids, such as polylysine; chitosan and polyethyleneimine. Examples of those high molecular weight polymers having carboxyl groups include poly(meth)acrylic acid, polyacrylic acid carboxymethylcellulose and alginic acid and the like. Examples of those high molecular weight polymers having sulfo group (or sulfate group) include heparin and polystyrene sulfonic acid and the like.

The low molecular weight compounds preferably have a molecular weight not greater than 200 daltons. More preferably the molecular weight of these compounds ranges from about 17 to about 120 daltons, inclusive. Examples of multi-functional low-molecular weight compound include lower alkylene diamine (e.g., ethylene diamine), glutaraldehyde and ethanedithiol, and the like.

Examples of functional groups substituted on the low molecular weight compound include an amino group which is covalently bondable with aldehyde (Schiff base which is formed from aldehyde group and amino group may further be reduced); an hydroxyl group and an amino group which are covalently bondable with carboxyl group; and carboxyl group and a sulfo group which are covalently bondable with hydroxyl group; or a mercapto group which is covalently bondable with amino group. Such a covalent bond can be formed under known reaction condition such as oxidation-reduction conditions, dehydration condensation conditions, addition conditions, and substitution (or displacement) conditions.

The high or low molecular weight compounds are reacted with the block copolymers using art recognized techniques. The block copolymers have functional groups on their ends, such as hydroxy, amino, carboxy, thio or may have leaving groups known in the art on their ends, such as halo, sulfonic acid esters, e.g., mesylate, tosylates, brosylates and the like. The high or low molecular weight compounds also have functional groups on their ends, e.g., hydroxy, amino, carboxy, thio, or may have on their ends leaving groups known in the art, such as halo, sulfonic acid esters, such as tosylates, mesylates, brosylates, and the like. The block copolymer is reacted with the high or low molecular weight compound under conditions effective to form a product. In this reaction, the product may be formed by displacement (substitution) or it may be formed under amide forming conditions, ester forming conditions, and the like, depending upon the functional groups present on the block copolymer as well as on the high or low molecular weight compound.

For example, in one embodiment, the chemistry can be represented by the following equation:

$$X_1\text{-}(A_1\text{-}B_1)\text{---}X_2+Y_1\text{---}R_x\text{---}Y_2 \rightarrow Y_1\text{---}R_x\text{---}Y_2\text{---}X_1\text{-}(A_1\text{-}B_1)\text{---}X_2\text{---}Y_1\text{---}R_x\text{---}Y_2$$

wherein ($A_1$-$B_1$-$A_1$-$B_1$) is a block copolymer;

$A_1$ is the hydrophilic segment;

$B_1$ is the hydrophobic segment;

$X_1$ and $X_2$ are the same or different and represent a group capable of forming a covalent bond with $Y_2$ and $Y_1$ respectively;

$Y_1$ and $Y_2$ are the same or different and represent a group capable of forming a covalent bond with $X_2$ and $X_1$ respectively; and $R_x$ is a low or high molecular weight compound.

For example, using this technique, the low or high molecular weight compounds can be bonded to the block copolymer through amide

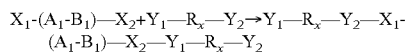

or ester linkages

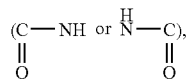

However, in a variation, only one of the X's (i.e., $X_1$ and $X_2$) is a leaving group, while the Y's (i.e., $Y_1$ and $Y_1$) are functional groups, such as hydroxy, thiol, amino, and the like. Under these circumstances, the reaction is as follows:

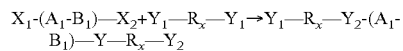

wherein $A_1$, $B_1$, $R_x$, $Y_1$ and $Y_2$ are as defined hereinabove, and $X_1$ and $X_2$ are leaving groups.

For example, using this method, the low or high molecular weight compounds can be bonded to the block copolymer through ether, thio, or amino bonds.

Similarly, if $X_1$ and $X_2$ are functional groups and $Y_1$ and $Y_2$ are leaving groups, then the following product is obtained:

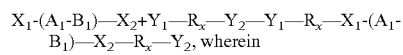

$A_1$, $B_1$, and $R_x$ are as defined above.

In another variation, $X_1$, $X_2$, $Y_1$, and $Y_2$ are leaving groups; in this way, carbon-carbon covalent bonds are formed between the block copolymer and the low or high molecular weight compounds:

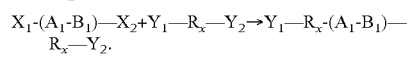

As indicated hereinabove, all of these reactions are effected under conditions sufficient to form desired product.

The same sort of reaction is effected with the surface, as described hereinbelow.

Figure 1:
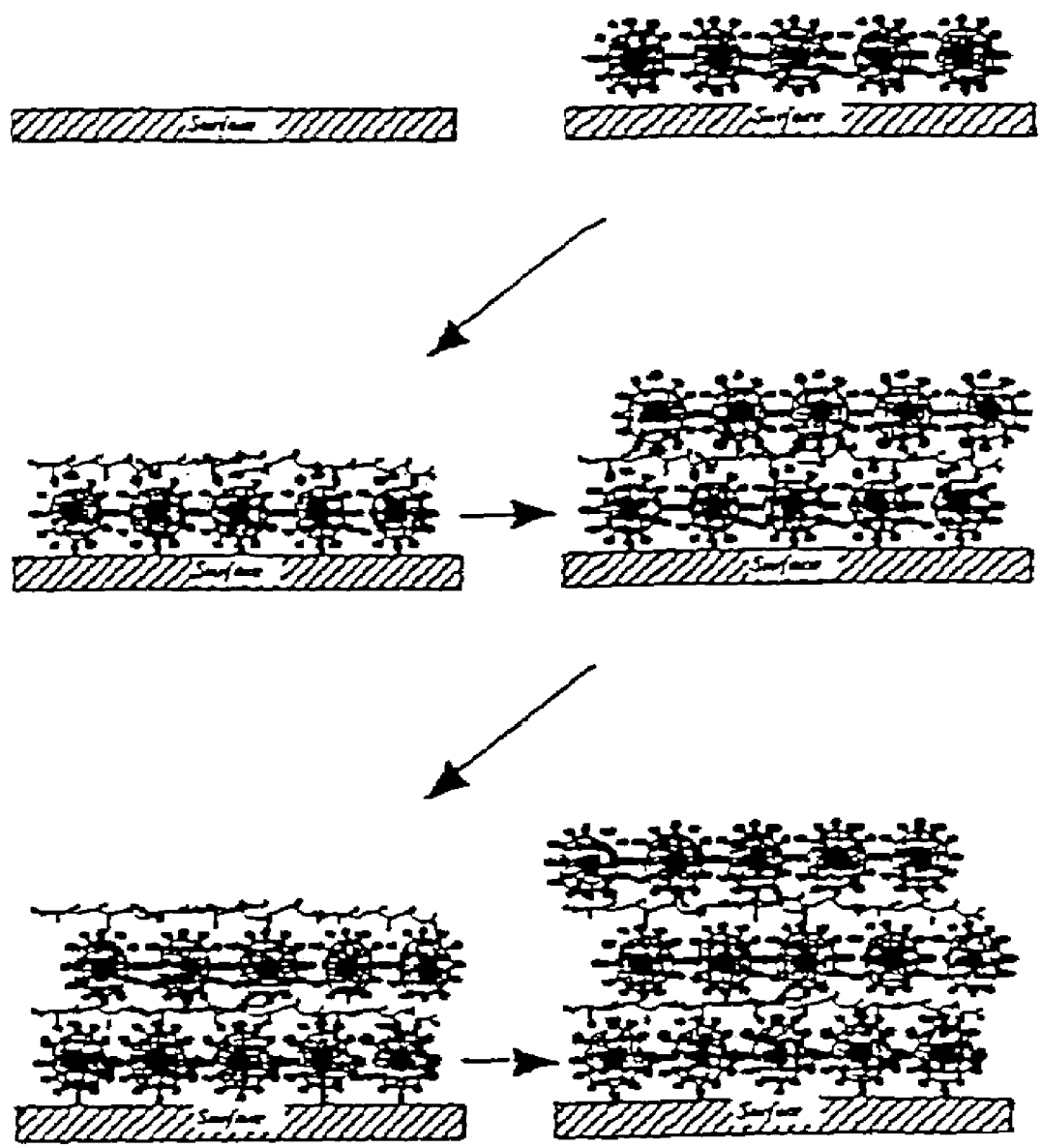
FIG. 1 is a schematic showing a polymer-micelle laminated surface and the lamination steps according to the present invention.

The support surface is made of e.g., glass, silicon wafer, polypropylene, etc. and it may also contain the above-mentioned functional groups. The support surface may be untreated or may be treated or modified as described herein. The support surface is coated with a micelle of the present invention. One layer of micelle may coat the support surface or it may be coated with more than one layer. If multi-layered, the micelle may contain a high molecular weight compound sandwiched between the layers. Alternatively, the micelle may contain a low molecular weight compound sandwiched between the layers. In another embodiment, the layers of the micelle may be crosslinked. Moreover, if there are more than 2 layers of micelle coating the support surface, the multi-level micelle may contain a combination of any of these embodiments. Furthermore, the support may be physically or chemically treated with a high-molecular weight polymer compound by a known method. An example of such a method is schematically illustrated in FIG. 1.

When the polymer micelle of the present invention is placed in water, a hydrogel is formed. The term "hydrogel" refers to a broad class of polymeric materials which are swollen extensively in water but which do not dissolve in water.

The polymer micelle of the present invention is produced by art recognized techniques or by using techniques described hereinabove or in any of the aforementioned patents and PCT applications, the contents of all of which are incorporated by reference.

The coating is then applied to the support surface. To ensure that the coating is immobile, it is preferred that the polymer micelle forms a covalent bond with the support surface. This may be effected by art recognized techniques such as by the following step:

(A) bringing a dispersion of the polymer micelle having functional groups on its surface into contact with the support surface which has on its surface other species of other functional groups which are reactive with the functional groups on the polymer micelle, and then permitting the respective functional groups on each of the support surface and the polymer micelle to react under conditions effective to form a covalent bond, and, if necessary, removing unreacted polymer micelle from thus formed covalently bonded matter.

If a multilayer coat is applied to the support surface, then step A described hereinabove is still utilized. However in the case of the multilayer coating, there are two additional steps also utilized in the process of coating the support surface:

(B) bringing the thus formed polymer micelle layer which has covalently been bonded with substrate into contact with a solution containing either a high-molecular weight polymer compound having a plural number of functional groups, as defined hereinabove or a multi-functional low-molecular weight compound having at least two, preferably two or three, functional groups as defined hereinabove, and accumulating on said polymer micelle layer either said high-molecular compound or said multi-functional low-molecular weight compound, and, then, reacting the functional group of the high molecular weight polymer compound or the low-molecular weight compound with the functional group on the polymer micelle of the product of step (A) under conditions effective to form a covalent bond, and, if necessary, removing unreacted high-molecular or low-molecular compound; and (C) bringing the thus obtained laminate of step (B) in which the high-molecular weight polymer compound or low-molecular weight compound has covalently been bonded into further contact with the aforementioned dispersion of the polymer micelle, accumulating said polymer micelle on the layer of said high-molecular weight polymer compound or multi-functional low-molecular weight compound of said laminate, and, then, covalently bonding said high-molecular or low-molecular weight compound with polymer micelle, and, if necessary, removing unreacted polymer micelle, and if necessary, further repeating said steps (B) and (C).

These reactions in B and C described hereinabove are conducted as described hereinabove.

The polymer micelle can be immobilized on a support surface of any geometry using free radical formation techniques such as electron beam radiation or UV or visible light in combination with a photoinitiator. According to this method, the polymer micelles are dissolved or suspended in an aqueous solution, preferably water, at a concentration sufficient to provide sufficient amount of polymer micelle to cover the support surface to the desired thickness. A preferred concentration ranges from about 0.5 mg/mL to about 15 mg/mL, inclusive and more preferably from about 1 mg/mL to about 5 mg/mL, inclusive. The resulting solution is then deposited onto the support surface, using techniques known in the art such as by spraying, spreading, immersing the support in the micellular solution, and the like. If the polymer micelle contains a polymerizable group, such as a carbon-carbon double bond, as in, for example, methacrylic acid, vinyl benzyl or ethylene, then the polymer micelle can be covalently bound to the support surface using techniques known to one of ordinary skill in the art.

Moreover, the surface of the support may be treated, prior to forming covalent linkages between the surface and the micelle.

The following illustrates the process. For example, as defined herein, a plasma prepared from hydrogen and nitrogen gas, such as 2 parts hydrogen gas and 1 part nitrogen gas, can be placed on the support as defined by the present invention. The plasma creates amino groups on the support surfaces. A polymer micelle having an aldehyde functionality can react with the surface under conditions of reductive amination to form a covalent bond with the support surface. Allylamine plasma is an alternative way to treat a substrate (or a medical device) surface to produce amine sites on the surface with which micelles can react. Instead of using hydrogen and nitrogen mixture, allylamine vapor is introduced into the plasma chamber, and this creates amino groups on the support surfaces, which can react with an aldehyde or keto group under reductive amination conditions.

Alternatively, if the micelle has carboxy groups thereon, the polymer micelle can react with the surface having amino groups under amide forming conditions.

Other functional groups may be placed on the substrate surface by coating the substrate with plasma containing said functional group. For example, the substrate can be coated with a plasma containing carboxy groups. Thus, if the micelle contains hydroxy groups, the plasma coated surface is reacted with the micelle under ester-forming condition to form an ester linkage between the micelle and the plasma coated surface. Alternatively, if the micelle contains amino groups, the micelle and the plasma coated surface react under amide forming conditions to form amide linkages between the micelle and the plasma coated surface.

It is to be noted that the carboxy groups may be placed on the surface by oxidizing the hydroxy groups thereon with oxidizing agents known to one skilled in the art to form carboxylic acids, which can then react with the hydroxy groups or amines on the micelles to form esters or amides, respectively, as described hereinabove. Thus, by exposing the surface to a reagent that affixes groups thereon which are reactive with the groups on the micelle (or high or molecular weight polymers or lower molecular weight compounds), the surface is activated to form a covalent bond with the micelle or (high molecular weight polymers or low molecular weight compound). Alternatively, the micelle may be exposed to a reagent that affixes groups thereon which are reactive with the functional groups on the surfaces. The polymer micelles in solution can be crosslinked together and to the surface by subjecting them to conditions which form free radicals, such as electron beam radiation, or addition of a photoinitiator and subsequent exposure to light or UV light which creates free radicals on the micelles. Crosslinking between the free radicals forms a covalent bond. Typically, if electron beam radiation is utilized, the solution containing the surface and polymer micelle is exposed to electron radiation in the range of between about one to about ten megarads, most preferably four megarads. Gamma radiation can be used as the radiation source but may result in the degradation of the polymer micelle unless oxygen is scrupulously excluded. Alternatively, a photoinitiator may be added to the solution and then the solution containing the photoinitiator and the polymer micelle are exposed to light or ultraviolet light of sufficient wavelength to form free radicals. Crosslinking via free radical coupling occurs randomly between the layers of the micelle and the surface. For example, in a preferred embodiment, the micelle consists of the PEO arms. If the PEO arms contain ethylenically unsaturated groups, then crosslinking can be effected by the techniques described hereinabove. Since the PEO contains several hydroxy groups, the terminal hydroxyl groups remain available for subsequent activation, such as for coupling affinity ligands to the PEO arms. Crosslinking enhances the stability of the micelle.

In another embodiment, the polymer micelle can be covalently immobilized to a support surface by tresylation of the terminal hydroxyl groups. The following embodiment is illustrative for a PEO hydrophilic group, but it is to be understood that this is only exemplary, and the techniques described hereinbelow are applicable to other hydrophilic groups.

The support surface and the polymer micelles are each pretreated prior to immobilization. As such, the support surface should contain active functional groups for immobilizing tresylated polymer micelles thereto, such as amino and/or thiol groups. Likewise, the polymer micelles are tresylated in an appropriate solvent prior to contacting with the support surface. Tresylation is particularly convenient for the PEO hydrophilic groups, since the PEO is solvated by media appropriate to tresyl chloride (e.g., dichloromethane, chloroform). This method results in a monolayer coating of the hydrogel over the support surface.

According to this method, an organic solvent, such as dichloromethane, comprising the polymeric micelle is exposed to tresyl chloride under conditions effective to affix the tresyl groups to the hydroxy-terminal on the PEO of the polymer micelle. The resulting tresylated PEO polymeric micelles are then precipitated and recovered, ultimately as a dry active product. Just prior to use, the tresylated PEO polymeric micelles are dissolved in an aqueous solution at a pH of ten or above, so as to favor reaction with amino and/or thiol groups already present on the support surface. The pH-adjusted solution is contacted with a support surface that contains amino and/or thiol groups, under conditions whereby the polymeric micelle become covalently bound in a dense layer to the support surface.

In addition to tresyl chloride, other reagents can be used to react with the terminal hydroxyl groups on the PEO chains. These reagents include tosyl chloride (p-toluene sulfonyl chloride), mesyl chloride (methane sulfonyl chloride), epichlorohydrin, cyanuric chloride ($C_3N_3Cl_3$), carbonyl diimidazole (CDI) and a mixture of succinic anhydride and succinimide. These reactions are generally described by Harris, "Laboratory Synthesis of Polyethylene Glycol Derivatives," *J. Macromolecular Sci. Reviews in Macro. Chem. Phys.*, C25(3), 325-373 (1985), the contents of which are incorporated by reference. For example, the hydroxy-terminated polyethylene oxide is reacted with tosyl chloride or mesyl chloride to form a tosylated or mesylated polymer micelle, respectively. In each case the activated PEO arms can be reacted with any molecule containing an amino or thiol group. By-products liberated by the reaction of the amino or thiol containing compound with the activated PEO arms include tresyl, mesyl or tosyl sulfonic acid, HCl (reaction of cyanuric chloride), imidazole (reaction of CDI), or N-hydroxylsuccinimide (reaction of succinic anhydride and succinimide). There is no by-product liberated in the epichlorhydrin reaction. Thus, any molecule containing an amino or thiol group, for example can become covalently attached to a tresylated, tosylated or mesylated polyethylene oxide chain by the formation of the stable NC or SC bond, with the elimination of the respective sulfonic acid, tresyl, tosyl or mesyl.

In another embodiment, the hydrophilic group may have carboxy groups thereon and the surface pretreated to form thereon amino or hydroxy groups. Then the surface and the polymer micelle are reacted under amide or ester forming conditions to form the corresponding amide or ester. Similarly, the surface may be modified to have free carboxy groups thereon, and the functional groups on the end of the polymer may be amino or hydroxy groups. Again, the micelle and the surface are reacted under amide or ester forming conditions to form the corresponding amide or ester, respectively. Moreover, the surface may be pretreated to have free hydroxy, amino or thiol groups. The polymer micelle has on its ends a leaving group, such as halide or sulfonic esters, e.g., brosylate, tosylate or mesylate and the like. The polymer micelle and the surface are reacted under displacement or substitution conditions to form the corresponding ether, amine or thio bonds. In another embodiment, if the surface has carbon-carbon double bonds and the end of the polymer micelle has carbon-carbon double bonds, then crosslinking may be effected by free radical reactions, using the techniques described herein. In this way, using common techniques in the art, the hydrophilic or hydrophobic core is bonded to the surface of the biomedical device through a covalent bond selected from the group consisting of

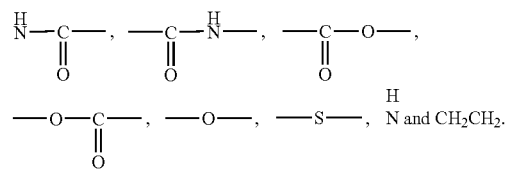

By coating the support, such as the biomedical device with the micelles comprised of the block copolymers having an HLB value ranging from about 1 to about 40, in accordance with the present invention, the biomedical device is substantially free of contaminants, especially proteins. Without wishing to be bound, it is believed that the micelles repel proteins, thereby keeping the surface of the biomedical device free of contaminants. This is especially useful when the biomedical device is inserted into the body of an animal, preferably mammal, such as dog, cat, cow, horse, and especially human. As a result, there is less contamination and less risk of infection when the inserted biomedical device is coated with the micelles described herein.

This invention provides a stable surface wherein the thickness of the hydrogel layer comprising polymer micelle is controlled within a range from several tens of nanometers to more than 100 nanometers.

The polymer micelle is useful as a carrier for guest systems, e.g. molecules. For example, the polymer micelle having a hydrophilic outer shell and a hydrophobic inner core can be a carrier in its interior with hydrophobic drugs which can then be released when the biomedical device is inserted into or placed into the body of the patient. The polymer micelle can be charged in its interior with the drug when said surface is contacted with said hydrophobic drugs in an aqueous solvent at an elevated temperature. The drugs are present in pharmaceutically effective amounts. Such drugs can slowly be released in an aqueous medium at ambient temperature. The present inventors have found that the rate of drug release is controlled by utilizing multi-layered micelle. More specifically, they have found that the more micelle Layers, the slower is the release of the drug. Thus, the present micelle system is capable at effecting controlled release of the drug. It is to be noted that drug charging may also be conducted by laminating a polymer micelle which has previously been charged with drug. It is preferably that the drug is adsorbed on the surface of the support. Regardless, the linkage of the drug to the surface of the support is biodegradable, that is, it is easily removed when inserted into the body of an animal. If the drug is covalently bonded to the surface, the covalent bond is such that it is hydrolyzed by the enzymes in the animal.

As used herein the term drug includes medicaments, therapeutics, vitamins, nutritional supplements, and the like.

The inventors have found that by coating the surface with the micelles described herein, the method provides a surface which exhibits excellent bioaffinity.

Any pharmaceutical drug can be utilized such as, for example, anti cancer drugs, drug for central nerves, drugs for peripheral nerve, drugs for allergy, drugs for circulatory organs, drugs for respiratory organs, drugs for digestive organs, hormone drugs, antibiotics, drugs for chemotherapy, vitamins, food supplements and the like.

Another application of the polymer micelles described herein is in the manufacture of contact lenses, especially contact lenses described in U.S. Pat. No. 4,680,336 to Larsen, et al., U.S. Pat. No. 4,889,664 to Kindt-Larsen, et al. and U.S. Pat. No. 5,039,459 to Kindt-Larsen, et al., the contents of all of which is incorporated herein by reference. For example, the contact lens prepared in accordance with the procedures of any of the aforementioned patents may be coated with the polymer micelle described herein. It may be coated with 1 layer or more than one layer. The polymer micelle can be covalently bound onto a suitable art recognized contact lens material such as a polyHEMA hydrogel contact lens described in U.S. Pat. Nos. 4,680,336, 5,039,459 and 4,889,664 using the techniques described herein. For example, the contact lens material can be immersed in a solution containing the polymer micelle and exposed to conditions forming free radicals ionizing radiation, as described hereinabove, to covalently bound the polymer micelle onto the contact lens surface. Alternatively, the surface of the contact lens material can be modified by creating amino or thiol groups on its surface. The modified lens material may then be exposed to an activated polymer micelle, such as the tresylated derivatives described hereinabove.

The contact lens material coated with the polymer micelle of the present invention has several advantages relative to those contact lens which are not coated with the micelles used herein. More specifically, due to the properties of the polymer micelle, absorption of proteineous deposits from natural enzymatic secretions of the eye by the coated lens material is substantially reduced or eliminated. Thus, the coated lenses will not become clouded or opaque because of lowered protein absorption.

In addition, the micelle of the present invention has the ability to reduce microbial, including bacterial contamination.

Moreover, the coated contact lenses have a greater ability to retain water and thus are less likely to dry out.

Furthermore, in accordance with the present invention, the contact lens so coated may be used as a carrier for guest molecules, such as a drug, in which the drug is covalently bound to the coated contact lens in accordance with the procedure described herein and then released from the contact lens through the eye into the body. Alternatively, the guest molecule, e.g., drug, is entrapped in the biomedical device. For example, the drug is incorporated into the material from which the biomedical device is prepared. Thus, for instance, if the biomedical device is a contact lens or an intraocular lens, the guest molecule, e.g., the drug is incorporated into the monomer mix, and cured into the lens in accordance with the procedure described in U.S. Pat. Nos. 4,680,336, 5,039,459 and 4,889,664. The drug is then released therefrom after insertion into the body of the animal, e.g., eye. Alternatively, the guest molecule may be associated with or entrapped inside the micelle or it may be covalently linked to the micelle. If entrapped in the micelle, the entrapped guest molecule is released after the insertion into the body of the animal. If covalently linked, just like as in case of the drug being covalently linked to the biomedical device, it is released by enzymatic cleavage (hydrolysis). Moreover, the release of drug molecules can be controlled, especially if multi-layers are utilized. Regardless, the guest molecule is present in amounts effective for its function. For example, if the guest molecule is a drug, it is present in therapeutically effective amounts relative to its function.

Thus, for example, the micelles described hereinabove can be used as a carrier for drugs to treat eye diseases. The drug is incorporated, as described hereinabove, onto the contact lens by techniques known in the art, and the contact lens so treated is coated with the micelle polymer described hereinabove. The contact lens with the coating and the drug is inserted into the eye. If controlled release is desired, the contact lens may be coated with a laminated micelle. When inserted into the eye, the enzymes present in the eye can cleave the micelle containing the drug, whereby the drug is delivered to the desired site.

In addition, when the drug is a mucin or a mucin-like structure, e.g., polylactides or polyglycolic acid, the micelle coating is useful as a carrier for treating dry eye syndrome.

Under normal conditions, ocular fluid forms a thin layer approximately 7-10 micrometers thick that covers the corneal and conjunctival epithelium. This ultra thin layer provides a smooth optical surface to the cornea by abolishing minute surface irregularities of its epithelium, wets the surface of the corneal and conjunctival epithelium, thereby preventing damage to the epithelial cells, and inhibits the growth of microorganisms on the conjunctiva in the cornea by mechanical flushing.

The tear film normally includes a three layer structure. The outermost layer is a lipid layer derived from the secretions of the meibomian glands and thought to retard evaporation of the aqueous layer. The middle aqueous layer is provided by the major and minor lacrimal glands, and contains water-soluble substances. The innermost mucinous layer is composed of glycoprotein mucin and overlies the corneal and conjunctival epithelial cells. The epithelial cell membranes are composed of lipoproteins and are thus generally hydrophobic. The mucin plays an important role in wetting the surface, as the aqueous tears to spread out on and the surface is wetted by a lowering of the tears' surface tension. Under normal conditions, mucin is provided by goblet cells of the conjunctiva and is also provided from the lacrimal gland.

When any of the tear film components is deficient, the tear film will break up, and dry spots will form on the corneal and the conjunctival epithelium. Deficiency of any of the three components (aqueous, mucin or lipid) may result in dryness of the eye. There are many forms of the disease known as keratoconjunctivitis sica. Those connected with rheumatoid arthritis or other connective tissue disease are referred to as Sjogren's syndrome.

The linkage between the drug and the contact lens is biodegradable. The mucin type products, e.g., polyglycolic acid or polylactides are hydrophobic and are thus soluble in the hydrophobic portion of the micelle. Thus, when the contact lens containing the drug and the micelle are inserted into the eye, the drug is easily removed from the contact lens by biological processes and the micelles hold the mucin-like material, which serves to wet the eye.

Besides the polylactides and polyglycolic acids, other mucin like material, such as collagen or gelatin can be adsorbed onto the contact lens, which is then coated with the micelle described hereinabove. The collagen and gelatin is also soluble in the micelle. When inserted into the eye, the collagen or gelatin is released from the contact lens, and wet the surface of the eye.

The mucin like material, e.g., polyglycolic acid, polylactides, collagen and gelatin is present in the coating in effective amounts.

As indicated hereinabove, the micelle of the present invention reduces microbial infection. For example, if the biomedical device is a contact lens or intraocular lens and if it is coated with the micelles of the present invention, the contact lens will have reduced microbial contamination. The micelle is present as a coating on the biomedical device in an amount sufficient to retard or prevent substantially contamination by the microbe.

However, to further reduce microbial (e.g., bacterial) contamination, the biomedical device or the micelle may be associated with an anti-microbial agent. The anti-microbial agent may be entrapped in the micelle or biomedical device, by, for example, being mixed in with material used to prepare the biomedical device. For example, if the biomedical device is a contact lens, the anti-microbial agent may be mixed in with the monomer e.g., polyHEMA, in accordance with the procedure described in U.S. Pat. Nos. 4,680,336, 5,039,459 and 4,889,664. Alternatively, it may be covalently bound to the biomedical device or micelle, using the techniques described herein. In this way, if the micelle or biomedical device contains an anti-microbial agent, there the contamination of the biomedical device, e.g., contact lens or intraocular lens, by microbes, e.g., bacteria, is reduced relative to a contact lens wherein the anti-microbial agent is absent. The anti-microbial agent is present on the coating device or in the micelle in an amount sufficient to retard and/or substantially prevent contamination by the microbe.

The present invention offers several advantages, especially when the hydrophilic moiety is PEG. One of the most important advantages is that a high density coating of a hydrophilic moiety, e.g., PEG can readily be obtained through simple micelle coating. This is not easy to achieve by PEG grafting to the surfaces. Without wishing to be bound, it is believed that this is attributable to the number of PEG chains in the micelle.

In addition, the present system prevents the flip flop of grafted PEG. This is a great advantage to keep the surface constant even in drastic change in the environment, for example, if the surface dries up. This migration of grafted chain into the sample interior upon drying is often a problem, especially for the treatment of surfaces with high mobility, including silicone. However, the coating of the present invention avoids this problem.

This invention is explained in more detail with the following examples. However, these examples are not intended to restrict this invention.

EXAMPLE 1

Production of acetal-terminated polyethylene glycol-polylactide block copolymer (Acet-PEG-PLA)

In an argon atmosphere, a reactor was charged with 30 ml of THF, 0.147 g of 3,3-diethoxypropanol and 3.0 ml of 0.34 mol/l solution of potassium naphthalene in THF, which were stirred for 10 minutes at room temperature. A potassium compound of 3,3-diethoxypropanol was thus formed. To the resultant solution, 7.04 g of ethylene oxide was added, and the resultant mixture was stirred at room temperature and at 1 atm. The resultant solution was allowed to react for two days, and then, 26.0 ml of 1.92 mol/l solution of DL-lactide in THF was added, and the resultant mixture was further stirred for two hours. Then, 3.1 g of methacrylic anhydride was added, and the resultant mixture was stirred for two days at room temperature. The resultant solution was poured into cooled 2-propanol, and the thus formed polymer was precipitated. The precipitate which was isolated by centrifugation was purified by freeze drying from benzene, with a yield of 11.48 g (79.4%). According to GPC and $^1$H-NMR, polyethylene glycol (PEG) segment, polylactide (PLA) and block copolymer had each a molecular weight of 5800, 4000 and 9800.

EXAMPLE 2

Preparation of Acet-PEG-PLA micelle and the conversion thereof into aldehyde PEG-PLA micelle In 40 ml of dimethyl acetamide (DMAc), there was dissolved 280 mg of the block copolymer which had been obtained in Example 1. The resultant solution was dialyzed against water (2 l: for 2 hours, 5 hours and 8 hours) using a dialysis membrane having a fractional molecular weight of 12-14000. To the resultant dialyzate, 1N-HCl was added to adjust the dialyzate to pH 2, and the resultant mixture was stirred for two hours. The resultant solution was adjusted to pH 7 by the addition of an aqueous solution of 0.1 N-NaOH. Then, the resultant solution was dialyzed against water for 24 hours using a dialysis membrane having a fractional molecular weight of 12-14000. The thus obtained dialyzate was transferred into a flask in an argon atmosphere, and, then 1.8 (w/w) % per micelle of potassium persulfate was added, and, after deaeration, the resultant mixture was allowed to react at 50° C. for 24 hours. The measurement of the dynamic light scattering (DLS) of the product indicated that the particle size and the indication μ/Γ 2 of polydispersion degree of the polymer micelle before and after the polymerization reaction were (35.5 nm, 0.094) and (41.0 nm, 0.125), respectively. Almost no change was seen in particle size between before and after the polymerization reaction.

To 2 ml of each of the solutions of the product before and after the polymerization reaction, there was added 1 ml of aqueous solution (20 g/l) of sodium dodecyl sulfate, and the resultant mixture was stirred for 24 hours, and was then subjected to DLS measurement. As a result, it was found that, although the polymer micelle before the reaction had almost completely disappeared, the polymer micelle after the reaction maintained a particle size and the indication μ/Γ 2 of polydispersion degree of 47.2 nm and 0.106 This shows that the polymer micelle after the reaction is so stable that it does not decompose even when treated with a surface active agent. Micelles before and after the polymerization reaction were freeze-dried, and subjected to $^1$H-NMR measurement in heavy chloroform. It was found that the peak (5.6 and 6.2 ppm), which was derived from the terminal olefin which had been seen before the reaction, completely disappeared, which suggests that polymerization had proceeded with efficiency. In this manner, the polymerization of the methacryloyl group at the end of polylactide gave a very stable micelle.

EXAMPLE 3

Preparation of Substrate (or Base Plate)

For the base plate, there was used a strip which is mainly made of slide glass, silicon wafer or polypropylene. Slide glass or silicon wafer was cut into a suitable size, and was subjected to ultrasonic cleaning, and, thereafter, was further cleaned in a mixed liquid at about 100° C. which was composed of 30% $H_2SO_4$ and $H_2O$ (at a volume ratio of 1:1), and was then rinsed fully with pure water. The thus treated fragment of slide glass or silicon wafer was dried in vacuum at normal temperature for 16 hours, and, then was dipped in a toluene solution of 3-aminopropyltriethoxysilane for 3 to 4 hours, and, thereafter, was dried in vacuum at 160° C. In this manner, the amino group was thereby introduced onto the surface of said fragment. When polypropylene was used as a material for the base plate, on the other hand, the amino group was introduced onto the surface of the base plate by means of a treatment (Samco International; Model BP-1; 75 W; 30 minutes) with plasma derived from $N_2:H_2$ (at a volume ratio of 1:2).

Measurement of $\zeta$ potential of the thus treated surface showed that the surface was positively charged in a low range pH. Hence, the presence of the amino group on surface was confirmed.

EXAMPLE 4

Polymer micelle Laminated Coat

Silicon wafer (made by Mitsubishi Material Co.) supporting an amino group on its surface which had been prepared in Comparative Example 3 was dipped, at a normal temperature for two hours, in a solution of a polymer micelle which had been obtained in accordance with the procedure of Example 2, having a concentration of about 1 mg/ml dissolved in 0.04 M HEPES [said solution containing 0.0032 (w/v) % NaCNBH$_3$]. After unbonded polymer micelles were removed by cleansing with pure water, the dipping in polymer micelle solution and cleaning were further repeated, and, thus, a laminated type micelle-gel membrane was constructed (See: FIG. 1). Incidentally, in the final micelle coating, NaCNBH$_3$ was used at a concentration of 0.25%.

EXAMPLE 5

Special Property Test of Laminated Membrane (polymer micelle layer; hereinafter called micelle coat)

(a) Measurement by Atomic Force Microscopy (AFM)

Figure 2:
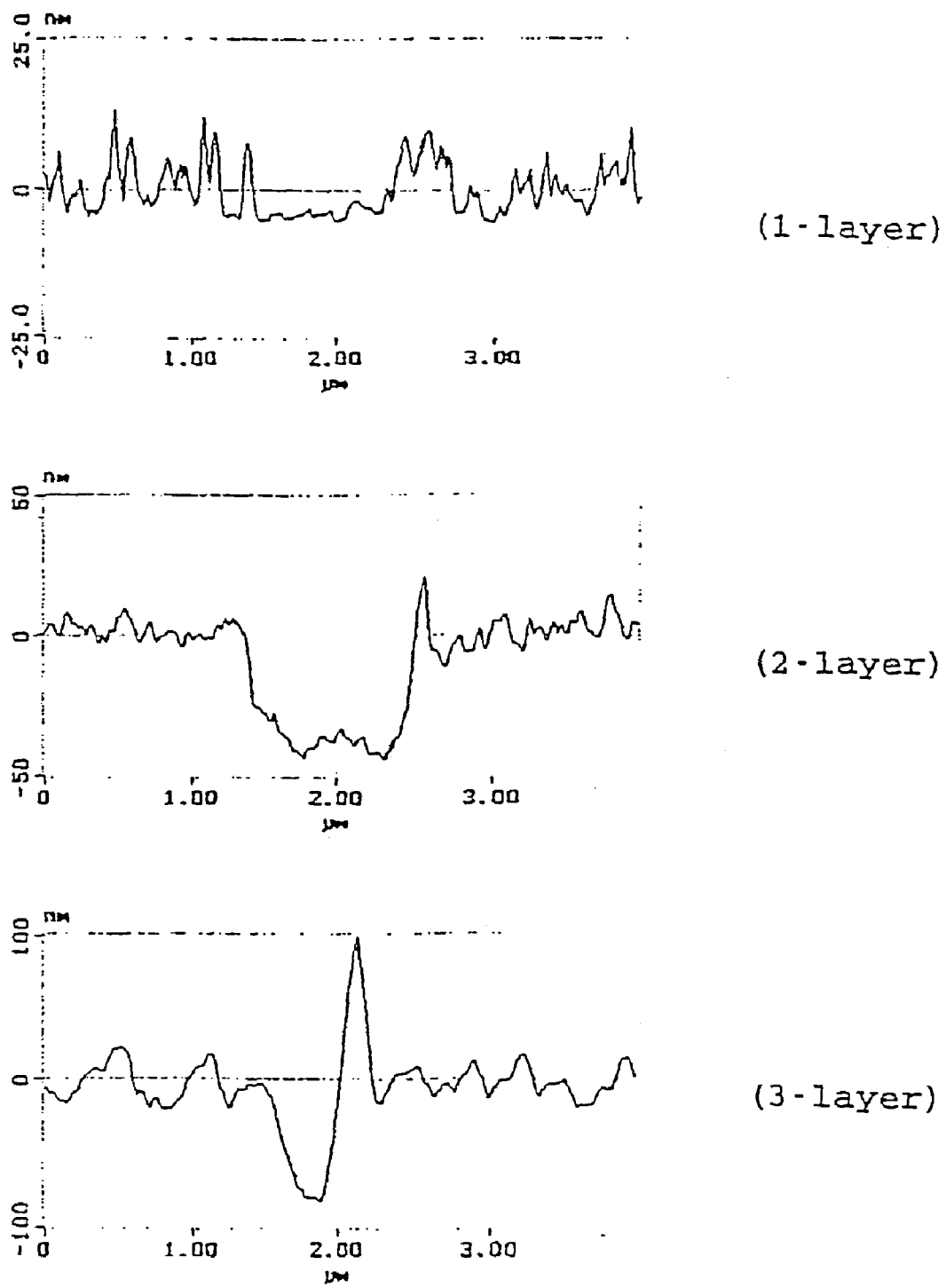
FIG. 2 is the AFM scanning of a shaved portion of a laminated polymer micelle surface.

The thickness of the micelle coat which had been prepared in Example 4 was examined with AFM. As for surface morphology, in the case of single coat, there was obtained an image wherein the micelle per se was immobilized on the surface. As the number of coated layers increases, however, there occurred variation, and irregularity became remarkable. An area of 1×1 μm$^2$ was shaved off from a surface coated with the multi-layered micelle, with a strong force of cantilever in contact mode, and, then, the cross section was examined in tapping mode. FIG. 2 shows the variation in thickness which was observed according to the number of coats. The thickness was about 20 nm in single coat, while it changed to 40-45 nm in the two-layer coat, and was 80-90 mm in the three-layer coat.

With regard to three-layer micelle coat, it was observed that the area shaved in the contact mode had decreased as time progressed. Without wishing to be bound, it is believed that in the laminated membrane on the surface, the micelle and polyallylamine had been crosslinked by a chemical bond; hence, the membrane which had been cut and compressed by cantilever gradually restored, resulting in the decrease of shaved area.

On the other hand, when a micelle whose core had not been polymerized (or, polymer micelle which had not been subjected to polymerization reaction) was three-layer coated for AFM examination, cracking was observed in the coated membrane. It is believed, without wishing to be bound that tension which had occurred in the membrane of the multi-layer coat led to the destruction of the membrane, whose core had not been polymerized, resulting in the formation of cracking. Incidentally, no such cracking was observed in the polymerized micelle.

(b) Measurement of $\zeta$ Potential.

Figure 3:
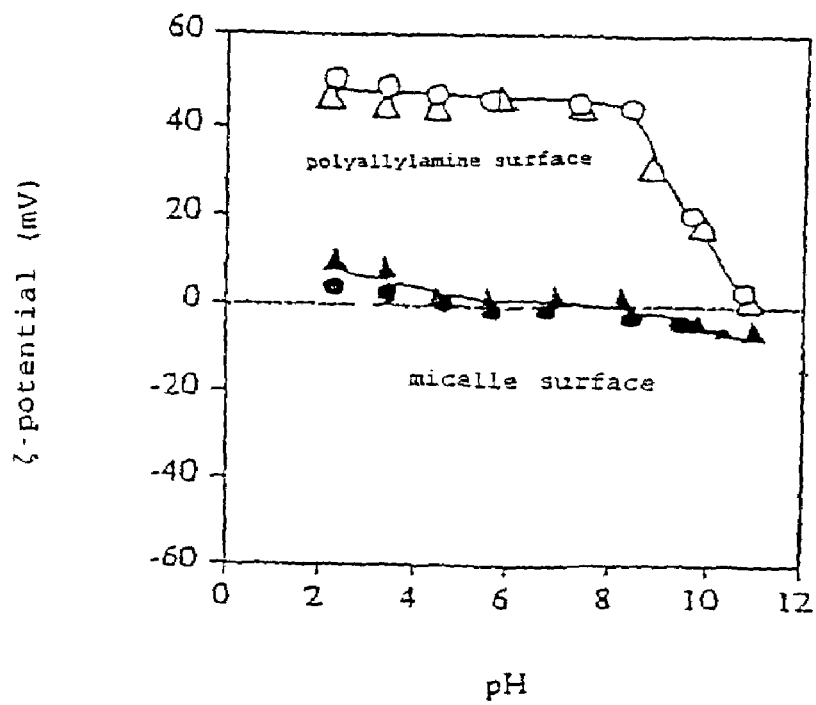
FIG. 3 graphically depicts the change in potential as a function of pH in a polymer micelle laminated surface.

Micelle surface of the above-mentioned micelle coat was measured for $\zeta$ potential in a 7.5 mM solution of sodium chloride in the range of pH 2 to 11. FIG. 3 shows the plots. When the micelle surface is the outermost surface, the change of the $\zeta$ potential caused by the variation of pH is as low as ±5 mV. When polyallylamine is on the outermost surface, on the other hand, the $\zeta$ potential was high as the pH increases up to pH 8, but when the pH increases higher than pH 8, the $\zeta$ potential decreases down to 0 at last. Up to three-layer coating, the $\zeta$ potential was unchanged regardless of lamination number, both in micelle surface and in polyallylamine surface. As is seen in FIG. 2, the thickness increases as lamination is repeated. As is seen in FIG. 3, although $\zeta$ potential differs largely between micelle layer and polyallylamine layer, only a small difference is caused by lamination number. This suggests that, although thickness increases by lamination, micelle layer and polyallylamine layer are not mixed with each other but instead are in a state of lamella-like layer.

(c) Protein Adsorption

Figure 4:
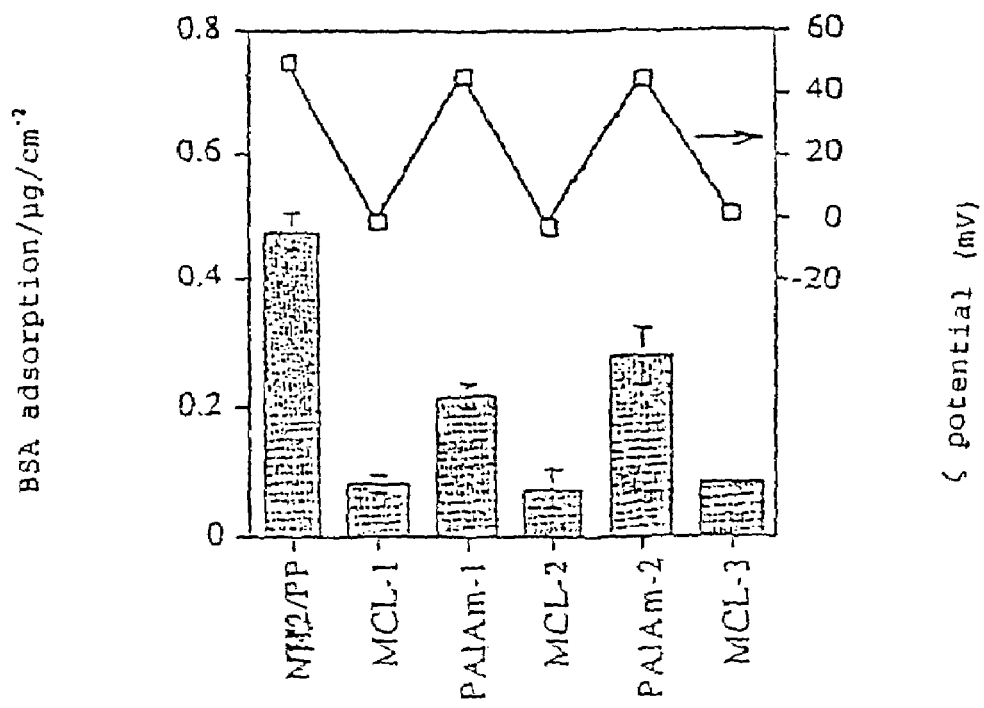
FIG. 4 graphically depicts the change in BSA adsorption property and in ζ potential, depending on polymer micelle lamination. In this graph, NH2/PP means plasma-treated polypropylene; MCL-1 means NH2/PP which has been coated with single layer of micelle; PAIAm-1 means MCL-1 which has been coated with polyallylamine; MCL-2 means PAIAm-1 which has been coated with micelle; PAIAm-2 means MCL-2 which has been coated with polyallylamine; and MCL-3 means PAIAm-2 which has been coated with micelle.

When a surface is coated with a hydrogel such as the above-mentioned micelle coat, in particular when the micelle is the outermost surface layer, it is expected that protein adsorption is inhibited. In order to confirm this, a surface of propylene base plate to which an amino group had been introduced in the above-mentioned way was coated with a micelle-laminated gel prepared in Example 1 and the adsorption of protein (bovine serum albumin: BSA) onto the micelle surface and polyallylamine surface was compared. The micelle-coated sample was dipped in a 45 μg/ml solution of BSA for one hour. After the sample was rinsed slightly, firmly adsorped protein was peeled with a surfactant (sodium dodecyl sulfate), and the thus peeled BSA was measured by the BCA method for the adsorption of BSA per unit volume (Anal., Biochem., 1985, 150, 76). The results are shown in FIG. 4. It was confirmed that, when the micelle is on the outermost surface, the adsorption of protein is inhibited. When polyallylamine is on the outermost surface, high protein adsorption is observed. Without wishing to be bounds it is believed that this phenomenon is attributable to the presence of positive charge on the sample surface resulting in the electrostatic interaction of the protein BSA which interacted with the positively charged surface of the poly(allylamine). However, when the surface was coated with the micelle, the reduced BSA adsorption indicates that the surface was fully covered with micelle which effectively masks the change of poly(allylamine).

In conclusion, the data clearly shows that the multi-layered coating of micelles works effectively in repelling proteins charged, the surface being positively charged, and the polyallylamine surface being slightly hydrophobic.

(d) Charging and Releasing of Pyrene into and out of Polymer Micelle

The hydrogel membrane is formed from the micelle prepared hereinabove. Thus, the hydrogel membrane contains a hydrophobic core membrane. As shown hereinbelow, it is possible, to charge a hydrophobic drug into the core interior of the gel surface which is formed from the micelle. As the data hereinbelow suggests, the release of the drug from the polymer micelle will be controlled release.

Pyrene was used as a model drug. A solution of pyrene in acetone was put in a flask, so that pyrene might be accumulated on the interior surface of flask. After well dried, the flask was charged with polymer micelle solution according to Example 2, which was stirred at 60° C. for four hours. After the temperature of the solution returned to a normal one, insoluble matters were then removed by a filter of 0.4 μm. The thus obtained pyrene-charged polymer micelle was then coated with different amounts of layers of the product of Example 1, ranging from one layer to six layers, in accordance with the procedure of Example 0.3. The specific coating is depicted in the following table:

TABLE 1

COATING OF MICELLE TO AMINATED GLASS SURFACE

| Samples | No. coatings | Coating Condition |
|---|---|---|
| ML2 | 1 | ~1 mg/mL-micelle with 0.25% (w/v) NaCNBH$_3$ in 0.01 MNaH$_2$PO$_4$, 25° C., 2 h |
| ML16 | 1 | ~1 mg/mL-micelle with 0.25% (w/v) NaCNBH$_3$ in 0.01 M NaH$_2$PO$_4$, 25° C., 16 h |
| 3LO | 3 | 1. ~1 mg/mL-micelle in 0.4 m HEPES (pH 6.7), 25° C., 2 h<br>2. 0.6% (w/v) polyallylamine in 0.04 M HEPES (pH 6.7), 25° C., 20 min.<br>3. Repeat 1 and 2 three times<br>4. ~1 mg/mL-micelle with 0.025% (w/v) NaCNBH$_3$ in 0.04 M HEPES (pH 6.7), 25° C., 40 h. |
| 3LE | 3 | 1. ~1 mg/mL-micelle with 0.0.016% (w/v) NaCNBH$_3$ in 0.04 M HEPES (pH 6.7), 25° C. 2 h<br>2. 0.6% (w/v) polyallylamine with 0.25% (w/v) NaCNBH$_3$ in 0.04 M HEPES (pH 6.7), 25° C., 2 h<br>3. Repeat 1 and 2<br>4. ~1 mg/mL-micelle with 0.025% (w/v) NaCNBH$_3$ in 0.04 M HEPES (pH 6.7), 25° C., 40 h |
| 6LE* | 6 | 1. ~1 mg/mL-micelle with 0.0.016% (w/v) NaCNBH$_3$ in 0.04 M HEPES (pH 6.7), 25° C., 2 h<br>2. 0.6% (w/v) polyallylamine with 0.25% (w/v) NaCNBH$_3$ in 0.04 M HEPES (ph 6.7), 25° C., 2 h<br>3. Repeat 1 and 2 three times<br>4. ~1 mg/mL-micelle with 0.025% (w/v) NaCNBH, in 0.04 M HEPES (pH 6.7), 25° C., 16 h. |

*The coating time for the third coat was overnight.

Figure 5:
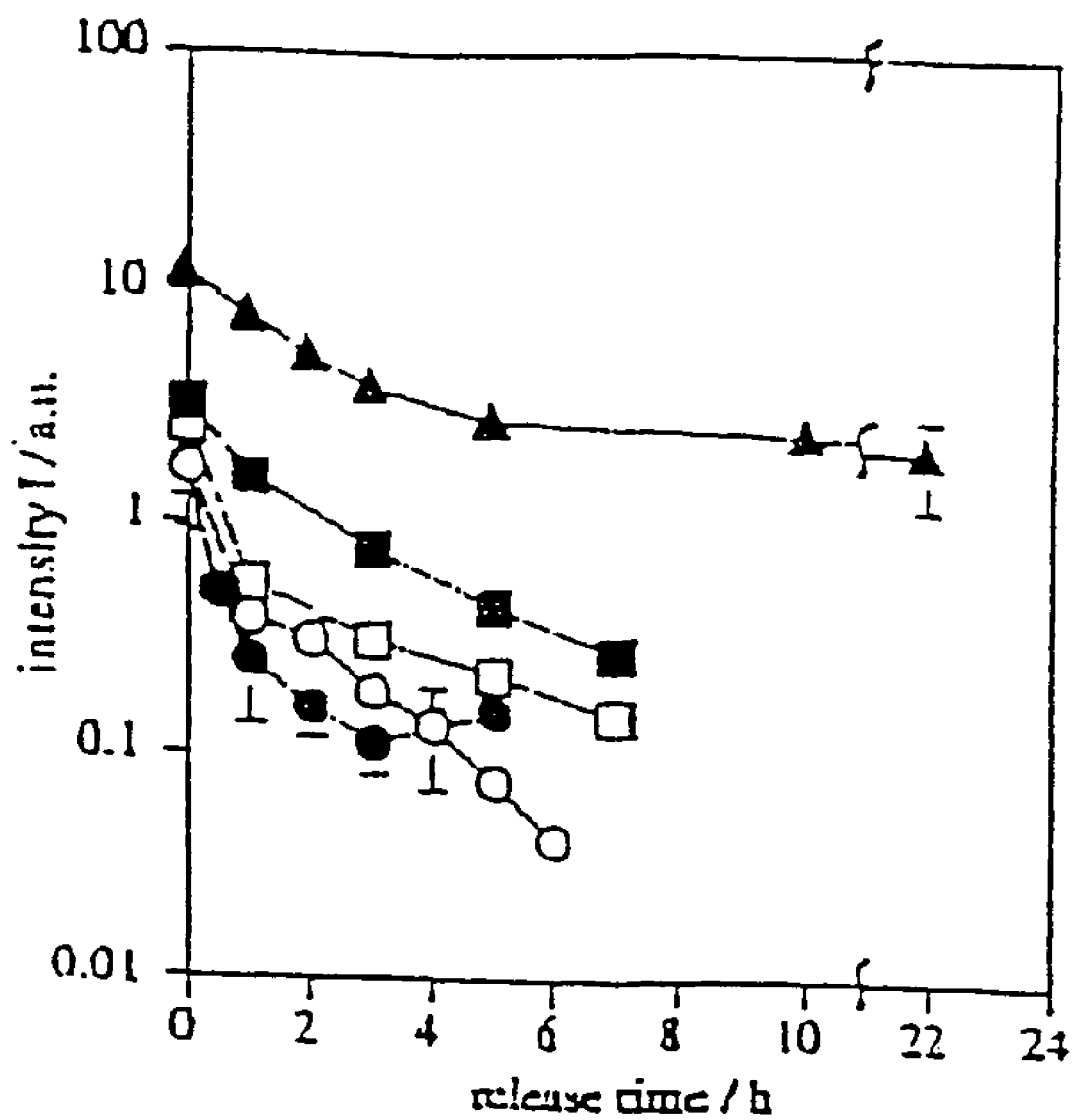
FIG. 5 graphically depicts the change in fluorescence intensity of ammonia plasma treated silica (APTS glass) coated with pyrene-incorporated micelle. In the graph, the following legend is utilized.

Each laminate was dipped in water, and was measured over time for the intensity of fluorescence caused by pyrene on the base plate. The results are shown in FIG. 5.

As shown by the data, the initial fluorescence intensity depends upon the number of coatings. The fluorescence of 3-time coating (3LO, 3LE) was twice as intense as the single coating (ML2, ML16), and 6-time coating (6LE) was about 10 times higher in intensity. This result indicates that by coating under the condition described in Table 1, the multilayer of micelle could be attached to the surface and the multi-layer increased the amount of pyrene on the surface.

The rate of fluorescence decline, on the other hand, depends upon the coating condition as well as the number of coatings. The initial fluorescence intensity seems to be closely correlated to the number of coatings. However, the differences in coating time (ML2 and ML16) and the differences in the reduction process of Schiff base (3LO and 3LE) resulted in a change in a decline rate of fluorescence as seen in FIG. 5. It should be noted that the 6-layer coating showed high initial intensity and the log-plot of intensity versus incubation time indicates a more controlled release of pyrene from the surface. Without wishing to be bound, it is believed that re-partitioning of the drug into the micelle during its diffusion through the multi-laminated micelle layer may have-occurred, allowing the achievement of extended drug release in a controllable manner.

(e) Loading and Release of Pyrene from Surface Coated Micelle

The loading of hydrophobic reagents after the coating of micelle was also investigated to determine if drugs can be reloaded repetitively into the micelle coated sample. For this purpose, the micelle coated sample prepared in Example 1 was exposed to pyrene containing micelle solution and water alternatively. The pyrene-free micelle solution was coated on APTS-glass under the same condition as 6LE. The micelle solution was coated on the APTS-glass under the same condition as 6LE. The micelle coated sample was then exposed to the pyrene-loaded micelle solution for 12 h. Then the sample was rinsed with water and stored in excess amount of water at room temperature (~22° C.) and at 4° C. for 12 h. During the storage, the fluorescence of the sample was measured periodically. After the storage in water, the sample was exposed to the pyrene-loaded micelle solution for 12 h and then water. FIG. 6 shows the plot of the fluorescence intensity ($\lambda$ex=336.2 nm, $\lambda$em –375 nm).

The fluorescence intensity after the exposure to pyrene-loaded micelle is almost identical to the initial intensity of 6LE in FIG. 5. After the first cycle (release-loading, 24 h), the fluorescence intensity was recovered to the initial level. The same was true with the second cycle. The first release (0-12 h) and the second release (24-36 h) showed similar decline in intensity. These results indicate that the micelle coating is stable and can load and release pyrene repetitively. The third exposure (48-60 h) was to 4° C. water. The decline in fluorescence intensity was slower than the first two releases (exposure to 22° C. water). Although the mobility of PLA segment may also affect the release of pyrene (hydrophobic drug) from the micelle, the temperature also may have also affected the diffusion coefficient of pyrene in the micelle. If the larger molecule than pyrene is loaded, the release rate is expected to be slower.

EXAMPLE 6

To evaluate the ability of micelle layers to prevent the free permeation of molecules, a polypropylene film (25 micron thick, 45% pore, ~0.25 micron pore size), PP, was used as a substrate. The film was covered with poly(hydroxyethyl methacrylate), PHEMA, by dipping the polypropylene film into a 10% solution in methanol and drying in ambient followed by the plasma treatment described herein. The aminated sample was coated with the monolayer micelle of Example 1 and the multi layered micelle of Example 4 as previously described. A permeation of dextran through the sample film was tested by measuring the diffusion of fluorescein isothiocyanate (FiTC) dextran (commercially available from Sigma Aldrich) from one side of the film through the other. The apparatus (4) utilized is shown in FIG. 7. The sample film (1) separates one side of the chamber filled with PBS solution (2) and the other side of the chamber which is filled with 0.1% (weight/volume) FITC dextran solution in PBS solution (3). The temperature of the chamber was set at 25° C. 3.0 mL of solution of the PBS was sampled every 24 hours and the rate of dextran permeation was determined by the change in its fluorescence intensity.

FIG. 8 shows the plot of the permeation of dextran through the micelle coated films. As a comparison, the permeation of the PP (polypropylene) film with PHEMA and the film with PHEMA treated with PEG-aldehyde under the same condition as the micelle coating is also shown. When the PHEMA/PP film is coated with PEG, the permeation of dextran increased. This is due to erosion of the PHEMA surface. The erosion is compensated by the monolayer micelle coating. The micelle coating effectively covered the surface. In the case of 3 layers of micelle coating, the permeation rate was remarkably prevented due to the formed network of micelle, polyallylamine (PAIAm; 10,000 MW, commercially available from Nittobo Chemical Company, Tokyo, Japan) and the increased thickness of the layer.

The above preferred embodiments and examples are given to illustrate the scope and spirit of the present invention. These embodiments and examples will make apparent to those skilled in the art other embodiments and examples. These other embodiments and examples are within the contemplation of the present invention.

Therefore, the present invention should be limited only by the appended claims.

What is claimed:

1. A coated biomedical device wherein the coating comprises at least one polymeric micelle immobilized to the surface of said biomedical device, said polymeric micelle being formed prior to the immobilization thereof to the surface of the biomedical device, said micelle having either a hydrophilic core and hydrophobic shell or a hydrophobic core and a hydrophilic shell, said micelle comprised of a block copolymer having a HLB value ranging from about 1 to about 40, wherein the biomedical device is a contact lens or an intraocular lens.

2. The coated biomedical device according to claim 1 wherein the HLB value of said block copolymer ranges from about 4 to about 20.

3. The coated biomedical device according to claim 1 wherein the micelle has an outer hydrophilic shell and an inner hydrophobic core.

4. The coated biomedical device according to claim 1 wherein the micelle has an outer hydrophobic shell and an inner hydrophilic core.

5. The coated biomedical device according to claim 1 wherein the micelle is covalently bonded to the surface of the biomedical device.

6. The coated biomedical device according to claim 5 wherein the micelle is bonded to the surface of the biomedical device through a covalent bond selected from the group consisting of

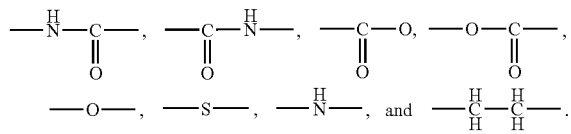

7. The coated biomedical device according to claim 1 wherein the micelle has a hydrophilic outer shell and a hydrophobic inner core and the hydrophilic outer shell is covalently bonded to the surface of the biomedical device.

8. The coated biomedical device according to claim 1 wherein the micelle has a hydrophobic outer shell and a hydrophilic inner core and the hydrophobic outer shell is covalently bonded to the surface of said biomedical device.

9. The coated biomedical device according to claim 7 wherein the hydrophilic shell consists essentially of a polyethylene glycol, polyacrylamide, polymethacrylamide, polyvinyl pyrrolidone, or polyvinyl alcohol.

10. The coated biomedical device according to claim 9 wherein the hydrophilic shell is a polyethylene glycol.

11. The coated biomedical device according to claim 7 wherein the hydrophobic inner core is methylmethacrylate, silicone, poly (α-hydroxycarboxylic acid) or poly (ω-hydroxycarboxylic acid).

12. The coated biomedical device according to claim 11 wherein the hydrophobic inner core comprises poly (α-hydroxycarboxylic acid) or poly (ω-hydroxycarboxylic acid) or methylmethacrylate.

13. The coated biomedical device according to claim 1 wherein the hydrophobic core has at its terminus a free radical reactive group.

14. The coated biomedical device according to claim 13 wherein said hydrophobic shell has at its terminus an ethyleneically polymerizable group.

15. The coated biomedical device according to claim 14 wherein the ethyleneically unsaturated polymerizable group is a free radical reactive polymerizable acrylate, free radical reactive polymerizable styryl, free radical reactive polymerizable methacrylate or a free radical polymerizable vinyl ethyl ether.

16. The coated biomedical device according to claim 1 wherein said hydrophilic core has at its terminus end a free radical reactive group.

17. The coated biomedical device according to claim 16 wherein said hydrophilic shell has at its terminus end an ethyleneically unsaturated polymerizable group.

18. The coated biomedical device according to claim 17 wherein the ethyleneically unsaturated polymerizable group is a free radical reactive polymerizable acrylate, free radical reactive polymerizable styryl, free radical reactive polymerizable methacrylate or a free radical polymerizable vinyl ethyl ether.

19. The coated biomedical device according to claim 1 wherein the biomedical device is coated with a monolayer of said micelle.

20. The coated biomedical device according to claim 1 wherein the biomedical device is coated with a multi-layer of said micelle.

21. The coated biomedical device of claim 20 wherein the biomedical device is coated with at most six layers of said micelle.

22. The coated biomedical device according to claim 20 wherein the multi-layer comprises at least one set of covalently bonded layers comprised of two polymer micelles and a second polymer sandwiched therebetween, said second polymer having a molecular weight greater than 8000 daltons, having a plural number of functional groups thereon selected from the group consisting of an amino group, a carboxyl group, and a sulfo group.

23. The coated biomedical device according to claim 22 wherein the second polymer is polyallylamine, polyvinylamine, polylysine, chitosan, polyethyleneimine, poly (meth) acrylic acid, carboxymethylcellulose, alginic acid, heparin, or polystyrene sulfonic acid.

24. The coated biomedical device according to claim 20, wherein at least two micelle layers are crosslinked to one another.

25. The coated biomedical device according to claim 20 wherein the biomedical device is coated with a multi-layer polymer micelle wherein the multi-layer comprises at least one set of covalently bonded layers comprised of two polymer micelles and sandwiched therebetween is a low molecular weight molecule selected from the group consisting of lower alkylene diamine, glutaraldehyde and ethanedithiol.

26. The coated biomedical device according to claim 1 wherein the block copolymer has the formula:

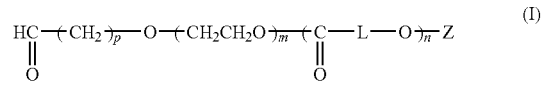

wherein
L denotes moieties of the following formula:

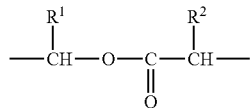

or —$(CH_2)_r$—
wherein
$R^1$ and $R^2$ independently denote hydrogen atom, $C_{1-10}$ alkyl, aryl or aryl-$C_{1-3}$ alkyl; r denotes an integer of 2-5, and wherein
m denotes an integer of 2-10,000;
n denotes an integer of 2-10,000;
p denotes an integer of 1-5; and
Z denotes acetyl, acryloyl, methacryloyl, cinnamoyl, allyl or vinylbenzyl.

27. the coated biomedical device according to claim 1 wherein the block copolymer has the formula:

wherein
X denotes an alkyl group having 1 to 10 carbon atoms which has an amino group, a carboxyl group or a mercapto group;
Y denotes moieties of the following formula:

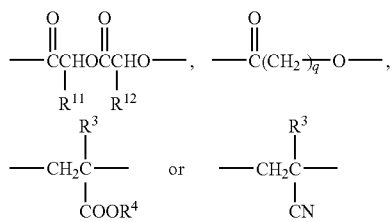

wherein
$R^{11}$ and $R^{12}$ independently denote a hydrogen atom or a $C_{1-5}$ alkyl;
$R^3$ denotes a hydrogen atom or a methyl group;
$R^4$ denotes a $C_{1-5}$ alkyl substituted by a hydroxyl group which may be protected; and
q denotes an integer of 2-5, and wherein
Z denotes acryloyl, methacryloyl, cinnamoyl, allyl or vinylhenzyl; m denotes an integer of 2-10,000; and
n denotes an integer of 2-10,000.

28. The coated biomedical device according to claim 1 wherein the block copolymer has the formula:

(III)

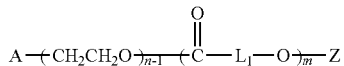

wherein
A denotes a group which is derived, by Malaprade oxidation, from a sugar residue having the following formula:

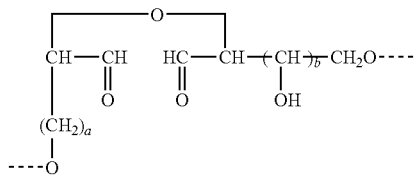

wherein
one of the broken lines (- - -) denotes a single bond while the other denotes a hydrogen atom; and
a and b independently denote an integer of 0 or 1, and wherein
$L_1$ denotes linking groups of the following formula:

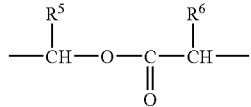

or —$(CH_2)_4$—
$R^5$ and $R^6$ independently denote a hydrogen atom, a $C_{1-6}$ alkyl, an aryl or a $C_{1-3}$ alkyl aryl; and
wherein
m denotes an integer of 2-10,000;
n denotes an integer of 2 10,000; and
Z denotes acryloyl, methyacryloyl, cinnamoyl, allyl or vinylbeuzyl.

* * * * *

UNITED STATES PATENT AND TRADEMARK OFFICE
CERTIFICATE OF CORRECTION

PATENT NO. : 7,674,478 B2
APPLICATION NO. : 10/653626
DATED : March 9, 2010
INVENTOR(S) : Kazunori Kataoka et al.

Page 1 of 1

It is certified that error appears in the above-identified patent and that said Letters Patent is hereby corrected as shown below:

In column 30, line 3, delete:

"vinylhenzyl" and replace with "vinylbenzyl"

In column 30, line 47, replace:

--vinylbeuzyl.-- and replace with "vinylbenzyl."

Signed and Sealed this
Fifth Day of April, 2011

David J. Kappos
*Director of the United States Patent and Trademark Office*